United States Patent
Gu et al.

(10) Patent No.: US 9,878,000 B2
(45) Date of Patent: *Jan. 30, 2018

(54) MUCOADHESIVE NANOPARTICLE COMPOSITION COMPRISING IMMUNOSUPPRESANT AND METHODS OF USE THEREOF

(71) Applicant: UNIVERSITY OF WATERLOO, Waterloo (CA)

(72) Inventors: Frank Xiaofei Gu, Kitchener (CA); Shengyan Liu, Waterloo (CA); Lyndon William James Jones, Waterloo (CA)

(73) Assignee: UNIVERSITY OF WATERLOO, Waterloo (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/142,709

(22) Filed: Apr. 29, 2016

(65) Prior Publication Data

US 2016/0243189 A1    Aug. 25, 2016

Related U.S. Application Data

(63) Continuation-in-part of application No. 13/923,274, filed on Jun. 20, 2013, and a continuation-in-part of
(Continued)

(51) Int. Cl.
*A61K 38/13* (2006.01)
*A61K 9/16* (2006.01)
(Continued)

(52) U.S. Cl.
CPC .............. *A61K 38/13* (2013.01); *A61K 9/006* (2013.01); *A61K 9/0048* (2013.01);
(Continued)

(58) Field of Classification Search
CPC ................ A61K 38/13; A61K 47/6937; Y10T 428/2982
See application file for complete search history.

(56) References Cited

U.S. PATENT DOCUMENTS

| 4,649,047 | A |   | 3/1987 | Kaswan |            |
|-----------|---|---|--------|--------|------------|
| 4,839,342 | A | * | 6/1989 | Kaswan | A61K 9/0048 |
|           |   |   |        |        | 424/450    |

(Continued)

FOREIGN PATENT DOCUMENTS

| CN | 101573141 A | 11/2009 |
| EP | 0 516 141 B1 | 8/1996 |

(Continued)

OTHER PUBLICATIONS

Verma, M. S., Liu, S., Chen, Y. Y., Meerasa, A., & Gu, F. X. (Jan. 2012). Size-tunable nanoparticles composed of dextran-b-poly (D, L-lactide) for drug delivery applications. Nano Research, 5(1), 49-61.*

(Continued)

*Primary Examiner* — Lakshmi S Channavajjala
(74) *Attorney, Agent, or Firm* — Brian C. Trinque; Lathrop Gage LLP

(57) ABSTRACT

Disclosed is a mucoadhesive nanoparticle delivery system for delivering an immunosuppressant, such as cyclosporine A, to a mucosal site for treatment of a disease or condition involving inflammation or excess immune activity. The system comprises nanoparticles formed from a plurality of linear amphiphilic block copolymers, each having a hydrophobic block comprising polylactide (PLA) and a hydrophilic block comprising dextran. The nanoparticles are surface-functionalized with a mucosal targeting moiety, such as a phenylboronic acid derivative, for targeted delivery and enhanced retention at the mucosal site. Pharmaceutical compositions, methods, and uses thereof comprising the
(Continued)

mucoadhesive nanoparticle delivery system are disclosed. The compositions can be administered in an effective amount for treating the disease or condition while substantially preserving or restoring the function and/or integrity of the mucosal lining. The composition may be formulated as an aqueous suspension for administration to an anterior surface of the eye in the treatment of dry eye syndrome.

20 Claims, 6 Drawing Sheets

Related U.S. Application Data application No. 14/410,521, filed as application No. PCT/CA2013/050475 on Jun. 20, 2013.

(60) Provisional application No. 62/156,474, filed on May 4, 2015, provisional application No. 61/690,127, filed on Jun. 20, 2012.

(51) Int. Cl.

| | |
|---|---|
| A61K 9/00 | (2006.01) |
| A61K 45/06 | (2006.01) |
| A61K 47/26 | (2006.01) |
| A61K 49/00 | (2006.01) |
| A61K 9/51 | (2006.01) |
| A61K 31/131 | (2006.01) |
| A61K 31/69 | (2006.01) |
| A61K 31/78 | (2006.01) |
| A61K 47/54 | (2017.01) |
| A61K 47/69 | (2017.01) |

(52) U.S. Cl.
CPC .......... *A61K 9/1647* (2013.01); *A61K 9/5123* (2013.01); *A61K 9/5153* (2013.01); *A61K 9/5161* (2013.01); *A61K 9/5192* (2013.01); *A61K 31/131* (2013.01); *A61K 31/69* (2013.01); *A61K 31/78* (2013.01); *A61K 45/06* (2013.01); *A61K 47/26* (2013.01); *A61K 47/54* (2017.08); *A61K 47/549* (2017.08); *A61K 47/6935* (2017.08); *A61K 47/6937* (2017.08); *A61K 47/6939* (2017.08); *A61K 49/0002* (2013.01); *Y10T 428/2982* (2015.01)

(56) References Cited

U.S. PATENT DOCUMENTS

| | | | |
|---|---|---|---|
| 6,007,845 A | 12/1999 | Domb et al. | |
| 6,254,860 B1 | 7/2001 | Garst | |
| 6,350,442 B2 | 2/2002 | Garst | |
| 6,525,145 B2 | 2/2003 | Gevaert et al. | |
| 7,803,392 B2 | 9/2010 | Mumper et al. | |
| 8,242,165 B2 | 8/2012 | Dash et al. | |
| 8,323,698 B2 | 12/2012 | Gu et al. | |
| 8,361,439 B1 | 1/2013 | Sung et al. | |
| 2004/0092435 A1* | 5/2004 | Peyman | A61K 9/0048 514/20.8 |
| 2005/0196440 A1 | 9/2005 | Masters et al. | |
| 2005/0281775 A1 | 12/2005 | Carrington et al. | |
| 2006/0263409 A1* | 11/2006 | Peyman | A61K 9/0051 424/427 |
| 2010/0006117 A1 | 1/2010 | Gutierrez | |
| 2010/0203142 A1 | 8/2010 | Zhang et al. | |
| 2010/0297007 A1 | 11/2010 | Lanza et al. | |
| 2010/0323199 A1 | 12/2010 | Gu et al. | |
| 2011/0104069 A1* | 5/2011 | Xu | A61K 9/0048 424/9.6 |
| 2011/0300219 A1 | 12/2011 | Lippard et al. | |
| 2013/0034602 A1 | 2/2013 | Qian et al. | |
| 2014/0005379 A1 | 1/2014 | Gu | |

| | | |
|---|---|---|
| 2014/0017165 A1 | 1/2014 | Wang et al. |
| 2015/0320694 A1 | 11/2015 | Gu |
| 2016/0243189 A1 | 8/2016 | Gu et al. |

FOREIGN PATENT DOCUMENTS

| | | |
|---|---|---|
| EP | 1 857 489 A1 | 11/2007 |
| EP | 1 652 517 B1 | 2/2012 |
| EP | 2 510 930 A1 | 10/2012 |
| JP | 3412198 B2 | 6/2003 |
| JP | 2011-140470 A | 7/2011 |
| WO | 1998/030207 A1 | 7/1998 |
| WO | 2000/048576 A1 | 8/2000 |
| WO | 2005/117844 A2 | 12/2005 |
| WO | 2007/124132 A2 | 11/2007 |
| WO | 2008/153966 A1 | 12/2008 |
| WO | 2010/096558 A1 | 8/2010 |
| WO | 2013/188979 A1 | 12/2013 |

OTHER PUBLICATIONS

Nouvel, C., Raynaud, J., Marie, E., Dellacherie, E., Six, J. L., & Durand, A. (2009). Biodegradable nanoparticles made from polylactide-grafted dextran copolymers. Journal of colloid and interface science, 330(2), 337-343.*
Raemdonck, K., Demeester, J., & De Smedt, S. (2009). Advanced nanogel engineering for drug delivery. Soft Matter, 5(4), 707-715.*
Missirlis et al. (2006) "Doxorubicin encapsulation and diffusional release from stable, polymeric, hydrogel nanoparticles," Eur. J. Pharm. Sci. 2:120-129.
Nagarwal et al. (2009) "Polymeric nanoparticulate system: A potential approach for ocular drug delivery," J. Controlled Release. 136:2-13.
Palumbo et al. (2006) "New graft copolymers of hyaluronic acid and polylactic acid: Synthesis and characterization," arbohydrate Polymers. 66(3):379-385.
Passirani et al. (1998) "Long-circulating nanoparticles bearing heparin or dextran covalently bound to poly(methyl methacrylate)," Pharm. Res. 7:1046-1050.
Peracchia et al. (1999) "Stealth (R) PEGylated polycyanoacrylate nanoparticles for intravenous administration and splenic targeting," J. Control. Release 1:121-128.
Pflugfelder et al. (2004) "Antiinflammatory Therapy for Dry Eye," American Journal of Ophthalmology. 137 (2):337-342.
Phillips et al. (1992) "Enhanced antibody response to liposome-associated protein antigens: preferential stimulation of IgG2a/b production," Vaccine. 10:151-158.
Portet et al. (2001) "Comparative biodistribution of thin-coated iron oxide nanoparticles TCION: Effect of different bisphosphonate coatings," Drug Dev. Res. 4:173-181.
Rehor et al. (2008) "Functionalization of polysulfide nanoparticles and their performance as circulating carriers," Biomaterials. 12:1958-1966.
Riley et al. (1999) "Colloidal stability and drug incorporation aspects of micellar-like PLA-PEG nanoparticles," Colloids Surf. B Biointerfaces. 16:147-159.
Riley et al. (2001) "Physicochemical evaluation of nanoparticles assembled from poly(lactic acid)-poly(ethylene glycol) (PLA-PEG) block copolymers as drug delivery vehicles," Langmuir. 11:3168-3174.
Sacco et al. (2010) "The Average Body Surface Area of Adult Cancer Patients in the UK: A Multicentre Retrospective Study," Plos One. 1:e8933-e8933.
Safra et al. (2000) "Pegylated liposomal doxorubicin (doxil): Reduced clinical cardiotoxicity in patients reaching or exceeding cumulative doses of 500 mg/m(2)," Ann. Oncol. 8:1029-1033.
Sakloetsakun et al. (2009) "In situ gelling properties of chitosan-thioglycolic acid conjugate in the presence of oxidizing agents," Biomaterials. 30:6151-6157.
Sall et al. (2000) "Two Multicenter, Randomized Studies of the Efficacy and Safety of Cyclosporine Ophthalmic Emulsion in Moderate to Severe Dry Eye Disease," Ophthalmology. 107(4):631-639.

(56) References Cited

OTHER PUBLICATIONS

Schmitz et al. (2008) "Synthesis and characterization of chitosan-N-acetyl cysteine conjugate," International Journal of Pharmaceutics. 347:79-85.
Shaikh et al. (Jan.-Mar. 2011) "Mucoadhesive drug delivery systems," J. Pharm. Bioallied Sci. 3(1):89-100.
Shen et al. (2010) "Thiolated chitosan nanopariticles enhance anti-inflammatory effects of intranasally delivered theophylline," Respir Res. 7(1):112.
Shen et al. (2010) "Thiolated nanostructured lipid carriers as a potential ocular drug delivery system for cyclosporine A: Improving in vivo ocular distribution," International Journal of Pharmaceutics. 402(1-2):248-253.
Shuai et al. (2004) "Micellar carriers based on block copolymers of poly(e-caprolactone) and poly(ethylene glycol) for doxorubicin delivery," J. Control. Release 3:415-426.
Sogias et al. (2008) "Why is Chitosan Mucoadhesive?" Biomacromolecules. 9:1837-1842.
Takeuchi et al. (2005) "Novel mucoadhesion tests for polymers and polymer-coated particles to design optimal mucoadhesive drug delivery systems," Advanced Drug Delivery Reviews. 57:1583-1594.
Unkeless et al. (1988) "Structure and function of human and murine receptors for IgG," Annu. Rev. Immunol. 6:251-281.
Yang et al. (2009) "Pharmacokinetics and biodistribution of near-infrared fluorescence polymeric nanoparticles," Nanotechnology 16:165101.
Yuan et al. (2006) "Preparation of cholesterol-modified chitosan self-aggregated nanoparticles for delivery of drugs to ocular surface," Carbohydrate Polymers. 65:337-345.
Zahr et al. (2006) "Macrophage uptake of core-shell nanoparticles surface modified with poly(ethylene glycol)," Langmuir. 19:8178-8185.
Zhong et al. (Sep. 2011) "[Synthesis and cell target recognition property of benzene boric acid modified amphiphilic block copolymers]," In; [The Abstracts of the National Polymer Academic Report, 2011]. [China Chemical Society of Polymer Science Committee]. Abstract No. F-0-18. p. 636—with English translation.
Zimmer et al. (1995) "Microspheres and nanoparticles used in ocular delivery systems," Adv. Drug Deliv. Rev. 1-6:61-73.
Advisory Action corresponding to U.S. Appl. No. 13/923,274, dated Oct. 18, 2016.
Office Action corresponding to Chinese Patent Application No. 201380040130.1, dated May 4, 2016—with English Translation.
Extended European Search Report corresponding to European Patent Application No. 138067293, dated Dec. 22, 2015.
International Preliminary Report on Patentability corresponding to International Patent Application No. PCT/CA2013/050475, dated Dec. 23, 2014.
International Search Report with Written Opinion corresponding to International Patent Application No. PCT/CA2013/050475, dated Sep. 27, 2013.
International Search Report with Written Opinion for International Patent Application No. PCT/CA2016/050500, dated Jul. 12, 2016.
Office Action corresponding to U.S. Appl. No. 13/923,274, dated Oct. 1, 2015.
Allen et al. (1991) "Pharmacokinetics of stealth versus conventional liposomes—effect of dose," Biochim. Biophys. Acta 2:133-141.
Allison (1998) "The Mode of Action of Immunological Adjuvantsm," Dev. Biol. Stand. 92:3-11.
Alpert (1990) "Hydrophilic-interaction chromatography for the separation of peptides, nucleic acids and other polar compounds," Journal of Chromatography A. 499:177-196.
Barber et al. (2005) "Phase III Safety Evaluation of Cyclosporine 0.1% Ophthalmic Emulsion Administered Twice Daily to Dry Eye Disease Patients for Up to 3 Years," Ophthalmology. 112(10):1790-1794.
Bazile et al. (1995) "Stealth Me.PEG-PLA nanoparticles avoid uptake by the mononuclear phagocytes system," J. Pharm. Sci. 4:493-498.

Bernkop-Schnurch (2001) "Improvement in the mucoadhesive properties of alginate by the covalent attachment of cysteine," Journal of Controlled Release. 71:277-285.
Chittasupho et al. (2009) SCAM-1 targeting of doxorubicin-loaded PLGA nanoparticles to lung epithelial cells, Eur. J. Pharm. Sci. 2:141-150.
Cho et al. (2008) "Therapeutic nanoparticles for drug delivery in cancer," Clin. Cancer. Res. 5:1310-1316.
Cholkar et al. (Dec. 5, 2012) "Novel Strategies for Anterior Segment Ocular Drug Delivery," Journal of Ocular Pharmacology and Therapeutics. 29(2):106-123.
Chouly et al. (1996) "Development of superparamagnetic nanoparticles for MRI: Effect of particle size, charge and surface nature on biodistribution," J. Microencapsul. 3:245-255.
Davidovich-Pinhas et al. (2010) "Novel mucoadhesive system based on sulfhydryl-acrylate interactions," J. Mater. Sci. Mater. Med. 21:2027-2034.
Dhar et al. (2008) "Targeted delivery of cisplatin to prostate cancer cells by aptamer functionalized Pt(IV) prodrug-PLGA-PEG nanoparticles," Proc. Natl. Acad. Sci. USA. 45:17356-17361.
Diebold et al. (2010) "Applications of nanoparticles in ophthalmology," Progress in Retinal and Eye Research. 29:596-609.
Dobrovolskaia et al. (2008) "Method for analysis of nanoparticle hemolytic properties in vitro," Nano Lett. 8:2180-2187.
Dong et al. (2007) "In vitro and in vivo evaluation of methoxy polyethylene glycol-polylactide (MPEG-PLA) nanoparticles for small-molecule drug chemotherapy," Biomaterials. 28:4154-4160.
Drummond et al. (1999) "Optimizing liposomes for delivery of chemotherapeutic agents to solid tumors," Pharmacol. Rev. 4:691-743.
Du Toit et al. (Jan. 2011) "Ocular drug delivery—a look towards nanobioadhesives," Expert Opin. Drug Derry. 8:71-94.
Ellis et al. (Feb. 3, 2012) "Boronate-mediated biologic delivery," Journal of the American Chemical Society. 134 (8)3631-3634.
Esmaeili et al. (2008) "Folate-receptor-targeted delivery of docetaxel nanoparticles prepared by PLGA-PEG-folate conjugate," J. Drug Target 5:415-423.
Fischer et al. (2003) "In vitro cytotoxicity testing of polycations: influence of polymer structure on cell viability and hemolysis," Biomaterials. 7:1121-1131.
Gaucher et al. (2009) "Effect of Poly(N-vinyl-pyrrolidone)-block-poly(D,L-lactide) as coating agent on the opsonization, phagocytosis, and pharmacokinetics of biodegradable nanoparticles," Biomacromolecules. 2:408-416.
Gaur et al. (2000) "Biodistribution of fluoresceinated dextran using novel nanoparticles evading reticuloendothelial system," Int. J. Pharm. 202:1-10.
Goodwin et al. (2009) "Phospholipid-dextran with a single coupling point: a useful amphiphile for functionalization of nanomaterials," J. Am. Chem. Soc. 1:289-296.
Gu et al. (2008) "Precise engineering of targeted nanoparticles by using self-assembled biointegrated block copolymers," Proc. Natl. Acad. Sci. USA. 7:2586-2591.
Guggi et al. (2004) "Matrix tablets based on thiolated poly(acrylic acid): pH-dependent variation in disintegration and mucoadhesion," International Journal of Pharmaceutics. 274:97-105.
He et al. (2010) "Effects of particle size and surface charge on cellular uptake and biodistribution of polymeric nanoparticles," Biomaterials. 13:3657-3666.
Jeong et al. (2011) "Doxorubicin-incorporated polymeric micelles composed of dextran-b-poly(DL-lactide-co-jlycolide) copolymer," Int. J. Nanomedicine. 6:1415-1427.
Jung et al. (2005) "Drug release from core-shell type nanoparticles of poly(DL-lactide-co-glycolide)-grafted dextran," J. Microencapsul. 22(8):901-911.
Kafedjiiski et al. (2006) "Improved synthesis and in vitro characterization of chitosan-thioethylamidine conjugate," Biomaterials. 27:127-135.
Karnik et al. (2008) "Microfluidic platform for controlled synthesis of polymeric nanoparticles," Nano Lett. 9:2906-2912.
Kataoka et al. (2001) "Block copolymer micelles for drug delivery: design, characterization and biological significance," Adv. Drug Deilv. Rev. 1:113-131.

(56) References Cited

OTHER PUBLICATIONS

Khutoryanskiy (Dec. 27, 2010) "Advances in Mucoadhesion and Mucoadhsive Polymers," Macromol. Biosci. 11:748-764.
Kim et al. (2005) "Interaction of PLGA nanoparticles with human blood constituents," Colloids Surf. B Biointerfaces. 2:83-91.
Kim et al. (Jan. 27, 2012) "Antitumor activity of sorafenib-incorporated nanoparticles of dextran/poly(dl-lactide-co-glycolide) block copolymer," Nanoscale Res. Lett. 7(1):91.
Kusnierz-Glaz et al. (1997) "Granulocyte colony-stimulating factor-induced comobilization of CD4(−)CD8(−) T cells and hematopoietic progenitor cells (CD34(+)) in the blood of normal donors," Blood. 7:2586-2595.
Lee et al. (2006) "Thiolated chitosan nanoparticles enhance anti-inflammatory effects of intranasally delivered theophylline," Resp. Res. 7:112.
Lee et al. (2010) "The effects of particle size and molecular targeting on the intratumoral and subcellular distribution of polymeric nanoparticles," Mol. Pharm. 4:1195-1208.
Li et al. (1997) "Biodegradable brush-like graft polymers from poly (D, L-lactide) or poly (D, L-lactide-co-glycolide) and charge-modified, hydrophilic dextrans as backbone-synthesis, characterization and in vitro degradation properties," Polymer. 38(25):6197-6206.
Li et al. (1998) "Biodegradable brush-like graft polymers from poly(D,L-lactide) or poly(D,L-lactide-coglycolide) and charge-modified, hydrophilic dextrans as backbone—in-vitro degradation and controlled releases of hydrophilic macromolecules," Polymer. 39:3087-3097.
Li et al. (2008) "Pharmacokinetics and biodistribution of nanoparticles," Mol. Pharm. 4:496-504.
Li et al.(Jan. 2012) "Low molecular weight chitosan-coated liposomes for ocular drug delivery: In vitro and in vivo studies," Drug Deliv. 19:28-35.
Liu et al. (Apr. 17, 2012) "Nanomaterials for Ocular Drug Delivery," Macromolecular Bioscience. 12:608-620.
Liu et al. (Sep. 11, 2014) "Phenylboronic Acid Modified Mucoadhesive Nanoparticle Drug Carriers Facilitate weekly Treatment of Experimentally-Induced Dry Eye Syndrome," Nano Research. 8(2):621-635.
Liu et al. (Nov. 20, 2012) "Development of mucoadhesive drug delivery system using phenylboronic acid functionalized poly(D,L-lactide)-b-dextran nanoparticles," Macromol. Biosci. 12(12):1622-1626.
Lorentz et al. (Dec. 24, 2011) "Contact lens physical properties and lipid deposition in a novel characterized artificial tear solution," Molecular Vision. 17:3392-3405.
Ludwig (2005) "The use of mucoadhesive polymers in ocular drug delivery," Adv. Drug Deliv. Rev. 57:1595-1639.
Magenheim et al. (1993) "A new in vitro technique for the evaluation of drug release profile from colloidal carriers—ultrafiltration technique at low pressure," Int. J. Pharm. 94:115-123.
Matsumoto et al. (2009) "Noninvasive Sialic Acid Detection at Cell Membrane by Using Phenylboronic Acid Modified Self-Assembled Monolayer Gold Electrode," J. Am. Chem. Soc. 131:12022-12023.
Matsumoto et al. (2010) "Assessment of Tumor Metastasis by the Direct Determination of Cell-Membrane Sialic Acid Expression," Angewandte Chemie—International Edition. 49:5494-5497.
Meerasa et al. (May 2011) "CH(50): A revisited hemolytic complement consumption assay for evaluation of nanoparticles and blood plasma protein interaction," Curr. Drug Deliv. 3:290-298.
U.S. Appl. No. 13/923,274, Office Action dated Dec. 16, 2016.
Gao et al. (Jan. 24, 2006) "Lectin-conjugated PEG-PLA nanoparticles: Preparation and brain delivery after intranasal administration," Biomaterials. 27:3482-3490.
Garinot et al. (Apr. 30, 2007) "PEGylated PLGA-based nanoparticles targeting M cells for oral vaccination," Journal of Controlled Release. 120:195-204.
Liu et al. (2010) "Synthesis of a linear copolymer Poly(lactic acid)-beta-dextran for drug delivery," In; The Abstracts of the XVIII International Conference on Bioencapsulation, Porto, Portugal, Oct. 1-2, 2010. Abstract No. O1-2. pp. 16-17.
Liu et al. (2010) "Synthesis of a linear copolymer Poly(lactic acid)-beta-dextran for drug delivery," In; The XVIII International Conference on Bioencapsulation, Porto, Portugal, Oct. 1-2, 2010. Presentation corresponding to Abstract No. O1-2, 16 pgs.
Liu et al. (2011) "Linear block copolymer Dextran-b-Poly(D,L-lactide) nanoparticles for ocular drug delivery," In; The Abstracts of the XIX International Conference on Bioencapsulation, Amboise, France, Oct. 5-8, 2011. Abstract No. O9-4. pp. 96-97.
Liu et al. (2011) "Linear block copolymer Dextran-b-Poly(D,L-lactide) nanoparticles for drug delivery applications," In; The XIX International Conference on Bioencapsulation, Amboise, France, Oct. 5-8, 2011. Presentation corresponding to Abstract No. O9-4, 15 pgs.
Liu et al. (Sep. 2012) "Mucoadhesive nanoparticles for topical ocular drug delivery," In; The Abstracts of the XX International Conference on Bioencapsulation, Orilla, Ontario, Sep. 21-24, 2012. Abstract No. P27. pp. 148-149.
Liu et al. (Sep. 2012) "Mucoadhesive nanoparticles for topical ocular drug delivery," In; The XX International Conference on Bioencapsulation, Orilla, Ontario, Sep. 21-24, 2012. Poster corresponding to Abstract No. P27, 1 pg.
Intention to Grant corresponding European Patent Application No. 13806729.3 with Granted Claims, dated Jun. 1, 2017.
Non-Final Rejection corresponding to U.S. Appl. No. 14/410,521, dated Mar. 13, 2017.
Notice of Reasons for Rejection corresponding to Japanese Patent Application No. 2015-517568, dated Apr. 10, 2017—provided with an English translation.
Office action corresponding to Chinese Patent Application No. 201380040130.1, dated Feb. 17, 2017—provided with an English translation.

\* cited by examiner

MUCOADHESIVE NANOPARTICLE COMPOSITION COMPRISING IMMUNOSUPPRESANT AND METHODS OF USE THEREOF

CROSS REFERENCE TO RELATED APPLICATIONS

This application is a continuation-in-part of U.S. patent application Ser. No. 13/923,274 filed Jun. 20, 2013, which claims the benefit of priority of U.S. Provisional Patent Application No. 61/690,127, filed Jun. 20, 2012. This application is also a continuation-in-part of U.S. patent application Ser. No. 14/410,521 filed Dec. 22, 2014 which is a U.S. National Entry of PCT Patent Application No. PCT/CA2013/050475, filed Jun. 20, 2013, which claims the benefit of priority of U.S. Provisional Patent Application No. 61/690,127, filed Jun. 20, 2012. This application also claims the benefit of priority of U.S. Provisional Patent Application No. 62/156,474, filed May 4, 2015. Each of the applications previously identified are hereby incorporated by reference in their entirely.

TECHNICAL FIELD

The present disclosure relates generally to a mucoadhesive nanoparticle composition comprising an immunosuppressant and methods of use thereof in administering an immunosuppressant to a mucosal site. In particular embodiments, the disclosure relates to a mucoadhesive nanoparticle composition comprising cyclosporine A and methods of use thereof in the treatment of dry eye syndrome.

BACKGROUND

Topical administration of therapeutic agents to mucosal tissues is desirable for several reasons. Mucosal delivery is generally non-invasive, thereby avoiding uncomfortable aspects of intravenous, intramuscular, or subcutaneous delivery that can reduce patient compliance. Topical administration to mucosal tissue can reduce the effect of first-pass metabolism and clearance by circulating immune cells, meaning that more drug reaches the target before being metabolized. Topical administration can also produce a predominantly localized effect thereby minimizing side effects associated with systemic drug circulation. However, given the tendency of natural fluids and secretions to clear the drug from the site of administration, topical administration to mucosal sites, such as the eye, nose and mouth, can be challenging.

Topical administration is the most common delivery method employed for treating diseases and conditions affecting the eye, such as dry eye syndrome (DES). DES is defined as a multifactorial disease affecting the tear film and the ocular surface that results in symptoms of discomfort, visual disturbance, and tear film instability with potential damage to the ocular surface. DES is also accompanied by increased osmolality of the tear film and inflammation of the ocular surface. Over 30 million people in the U.S. exhibit dry eye syndrome (DES). Of these, 4.8 million have moderate to severe DES and use Restasis® (Allergan Inc., Irvine, Calif.), an ophthalmic emulsion comprising 0.05% wt/vol cyclosporine A (CsA, an immunosuppressant). Restasis® is the first commercially-available eye drop formulation that showed an increase in natural tear production in dry eye patients, in part by acting to reduce inflammation and concurrent loss of the conjunctival epithelium and goblet cells.

Eye drops, such as Restasis®, are the most popular method of delivering therapeutics to the eye due to their convenience and non-invasiveness. However, their biggest challenge is rapid clearance due to tear dilution and turnover: more than 95% of the administered drugs are cleared before they reach their intended target. Hence, eye drop formulations often must be administered frequently (twice daily for Restasis®, but up to four times for many topical drugs) and at high doses so that the drug concentrations may reach the therapeutic window. The requirement for frequent dosing reduces patient compliance. Furthermore, the high overall dosage of the administered drugs results in increased side effects: approximately 25% of people in a phase III safety evaluation of Restasis® reported experiencing one or more adverse effects such as burning, stinging and foreign body sensation on the ocular surface (Sall et al. 2000; Barber et al., 2005). Since DES requires constant long-term treatment of its symptoms, reducing the dosage of CsA using a more efficient drug delivery platform is desired and may likely reduce side effects and improve patient compliance, without compromising therapeutic efficacy. In addition, lower administration rates would reduce the likelihood for adverse reactions to the preservatives that are commonly included in topical formulations and which are a common cause of ocular surface damage.

Nanoparticles (NP) as drug carriers have been proposed to address the challenges associated with conventional eye drop delivery methods. By encapsulating drugs as their cargo, NPs may increase the concentration of drugs in the formulation, control the release rates of the drugs, and improve corneal retention by targeting the ocular surface. The controlled release of drugs from the NP drug carriers may also reduce the total amount of drug exposed on the ocular tissue at any given time, thus reducing the risk of side effects. Moreover, the small size of the NP (particle sizes 10 µm) eliminates discomfort experienced by users from administration of larger particles. Certain NP formulations may also be tuned to achieve transparency and viscosity similar to that of water. A number of polyester based polymers, such as poly(lactic-co-glycolic acid) (PLGA), poly(glycolic acid) (PGA), poly(ε-caprolactone) (PCL), and poly(lactic acid) (PLA) have been explored as suitable materials for preparing a NP drug delivery platform for targeting eye diseases. These NPs have been coated with polyethylene glycol (PEG) to improve their colloidal stability.

Recently, the present inventors developed an amphiphilic block copolymer composed of poly(D,L-lactic acid) and dextran (PLA-b-Dex) to formulate NP drug carriers (Verma et al., 2012). US 2014/0005379, entitled "Nanoparticle delivery system and components thereof", describes nanoparticles formed from amphiphilic block copolymers comprising polylactide and dextran as drug delivery system. Dextran is conjugated to a targeting moiety in a manner that the surface of the nanoparticle is coated with the targeting moiety. The size and the targeting of the nanoparticles can be tuned by controlling the surface density of the targeting moiety.

Dextran provides a unique advantage over PEG-based materials due to its greater hydrophilicity and significantly higher density of functional groups for surface modification. Furthermore, dextran based NPs have previously demonstrated superior colloidal stability compared to PEG based NPs. Dextran has three hydroxyl groups per monomer, whereas PEG only has one functional end group per chain: increased functional groups improves the efficiency of surface modification and consequently provides greater control over the surface properties of the NPs. Previously, the present inventors modified the surface of PLA-b-Dex NPs with phenylboronic acid (PBA) molecules to achieve mucoadhesion through covalent linkage between PBA and the cis-diol groups of carbohydrates abundant on the ocular mucous membrane (Liu et al. 2012). By covalent attachment, PBA-modified NPs provide a greater affinity towards mucous membranes compared to the more commonly studied mucous-targeting molecules, such as chitosan, which rely on physical interaction with the mucous membrane.

Since the NPs target the surface mucous membrane, the rate of clearance of the NPs is likely reflected by the turnover rate of the ocular mucous membrane. The present inventors previously demonstrated significantly improved mucoadhesive properties using PBA-modified NPs, compared to Chitosan-based or thiol-based NPs, and a sustained release of CsA for up to 5 days. It was further demonstrated that the CsA-loaded NPs were biocompatible on rabbit eyes, and were effective in treating dry eye conditions in a short term study on mice (Liu et al. 2014). The effects of chronic treatment in a dry eye model were not examined.

It is desirable to provide improved compositions and methods for topical administration of therapeutic agents to mucosal tissues.

SUMMARY OF THE DISCLOSURE

It is an object of the present disclosure to obviate or mitigate at least one disadvantage of previous compositions and methods for topical administration of therapeutic agents to mucosal tissues.

In a first aspect, the present disclosure provides a method for treating a disease or condition involving inflammation, comprising topically administering a pharmaceutical composition to a mucosal surface of a subject, the composition comprising nanoparticles capable of releasing an immunosuppressant, the nanoparticles comprising a plurality of linear amphiphilic block copolymers including a hydrophilic block and a hydrophobic block, the hydrophobic block comprising polylactide (PLA) and the hydrophilic block comprising dextran (Dex), the nanoparticles being functionalized with a mucosal targeting moiety.

In another aspect, there is provided a method for hydrating a mucosal surface comprising topically administering to the mucosal surface a pharmaceutical composition comprising nanoparticles, the nanoparticles comprising a plurality of linear amphiphilic block copolymers each including a hydrophilic block and a hydrophobic block, the hydrophilic block comprising dextran (Dex) and the hydrophobic block comprising polylactide (PLA), the nanoparticles being functionalized with a mucosal targeting moiety.

In another aspect, there is provided a topical pharmaceutical composition for the treatment of dry eye syndrome, the composition being an aqueous suspension for administration to the anterior surface of the eye, the composition comprising nanoparticles capable of releasing cyclosporine A, the nanoparticles comprising a plurality of linear amphiphilic block copolymers including a hydrophilic block and a hydrophobic block, the hydrophobic block comprising polylactide (PLA) and the hydrophilic block comprising dextran (Dex), the nanoparticles being functionalized with a mucosal targeting moiety, wherein the concentration of cyclosporine A in the composition is about 0.001% to about 0.1% wt/vol, and wherein the composition is formulated for administration of cyclosporine A at an overall dose of less than about 150.0 µg per week and an administration frequency of less than 10 times per week.

In another aspect, there is provided a pharmaceutical composition for use in treating a disease or condition capable of being treated via topical administration of an immunosuppressant to a mucosal site, the pharmaceutical composition comprising nanoparticles capable of releasing an immunosuppressant, the nanoparticles comprising a plurality of linear amphiphilic block copolymers including a hydrophilic block and a hydrophobic block, the hydrophobic block comprising polylactide (PLA) and the hydrophilic block comprising dextran (Dex), the nanoparticles being functionalized with a mucosal targeting moiety, wherein the pharmaceutical composition is administered in an effective amount capable of treating the disease or condition while substantially preserving or restoring the function and/or integrity of the mucosal lining.

In another aspect, there is provided a topical pharmaceutical composition for use in the treatment of dry eye syndrome, the composition being an aqueous suspension for administration to the anterior surface of the eye, the composition comprising nanoparticles capable of releasing cyclosporine A, the nanoparticles comprising a plurality of linear amphiphilic block copolymers including a hydrophilic block and a hydrophobic block, the hydrophobic block comprising polylactide (PLA) and the hydrophilic block comprising dextran (Dex), the nanoparticles being functionalized with a mucosal targeting moiety, such as such as a derivative pf phenylboronic acid (PBA), wherein the composition is formulated for administration of cyclosporine A at an overall dose of less than about 150.0 µg per week at an administration frequency of less than 10 times per week, such as, once per day or once per week.

In another aspect, there is provided a use of a mucoadhesive nanoparticle composition comprising cyclosporine A in the manufacture of a medicament for treating a disease or condition capable of being treated via topical administration of cyclosporine A to a mucosal site, the nanoparticles capable of releasing cyclosporine A, the nanoparticles comprising a plurality of linear amphiphilic block copolymers including a hydrophilic block and a hydrophobic block, the hydrophobic block comprising polylactide (PLA) and the hydrophilic block comprising dextran (Dex), the nanoparticles being functionalized with a mucosal targeting moiety, wherein the pharmaceutical composition is administered in an effective amount capable of treating the disease or condition while substantially preserving or restoring the function and/or integrity of the mucosal lining.

In further aspect, the present disclosure provides a pharmaceutical composition for use in hydrating a mucosal lining, such as a mucosal lining of the eye, the composition comprising nanoparticles, the nanoparticles comprising a plurality of linear amphiphilic block copolymers including a hydrophilic block and a hydrophobic block, the hydrophobic block comprising polylactide (PLA) and the hydrophilic block comprising dextran (Dex), the nanoparticles being functionalized with a mucosal targeting moiety, such as a derivative pf phenylboronic acid (PBA), the composition optionally further comprising an immunosuppressant.

Other aspects and features of the present disclosure will become apparent to those ordinarily skilled in the art upon review of the following description of specific embodiments in conjunction with the accompanying figures.

BRIEF DESCRIPTION OF THE DRAWINGS

Embodiments of the present disclosure will now be described, by way of example only, with reference to the attached Figures.

Figure 1:
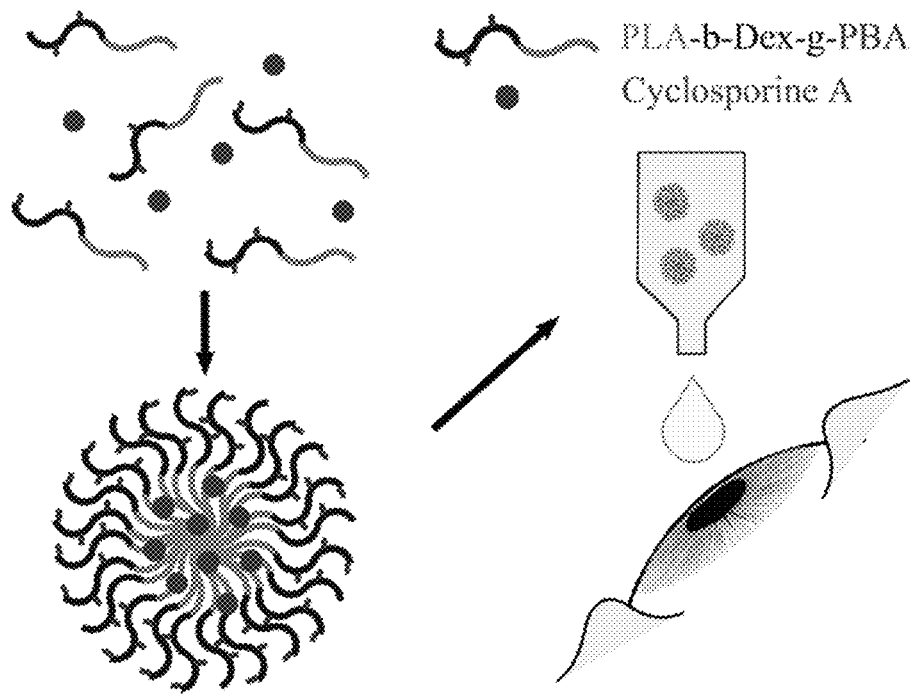
FIG. 1. Schematic illustration of mucoadhesive nanoparticles delivering immunosuppressant to the ocular surface through eye drop administration. PLA-b-Dex-g-PBA represents the polymer precursor used for the assembly of the nanoparticle eye drop drug carriers. Cyclosporine A is a commonly used immunosuppressant used for treatment of dry eye diseases.

In the drawings, preferred embodiments of the invention are illustrated by way of example. It is to be expressly understood that the description and drawings are only for the purpose of illustration and as an aid to understanding, and are not intended as a definition of the limits of the invention.

DETAILED DESCRIPTION

Generally, the present disclosure relates to a mucoadhesive nanoparticle composition comprising an immunosuppressant and methods of use thereof in administering an immunosuppressant to a mucosal site. The mucoadhesive nanoparticle composition and methods disclosed herein may be useful in the treatment of diseases and conditions capable of being treated via topical administration of an immunosuppressant to a mucosal site, such as a disease or condition involving inflammation or excessive immune activity. As used herein, a "mucosal site" refers to an area of the body comprising tissue that contains a mucosal lining (or mucosal surface), such as the eye, mouth, ear, nose, esophagus, bronchia, stomach, intestine, rectum, vagina, urethra, penis or uterus. In some embodiments, the disease or condition to be treated is dry eye syndrome.

The mucoadhesive nanoparticle nanoparticles described herein are capable of delivering an immunosuppressant to a mucosal site. The nanoparticle delivery system was described previously in WO 2013/188979, to the present inventors, entitled "Mucoadhesive nanoparticle delivery system", also published as US 2015/0320694, both of which are incorporated herein by reference in their entirety. The nanoparticles are formed from amphiphilic block copolymers comprising a hydrophilic portion and a hydrophobic portion. The block copolymers are capable of self-assembly to form nanoparticles according to methods well known to those skilled in the art, including nanoprecipitation methods. For example, in an aqueous environment, amphiphilic diblock copolymers will assemble into a core-shell type of nanoparticle with a hydrophobic core and a hydrophilic shell. Such nanoparticles are particularly useful for carrying hydrophobic payloads. The nanoparticles are capable of carrying a wide variety of payloads and demonstrate good loading capacity and loading efficiency.

In some embodiments, the copolymer is an amphiphilic diblock copolymer having a hydrophilic portion and a hydrophobic portion connected end-to-end in a linear fashion. In some embodiments, the hydrophilic portion of the diblock copolymer comprises dextran. In some embodiments, the hydrophobic portion of the diblock copolymer comprises polylactide (PLA). In some embodiments, the hydrophilic portion of the diblock copolymer consists essentially of dextran. In some embodiments, the hydrophobic portion of the diblock copolymer consists essentially of polylactide (PLA). In one embodiment, the diblock copolymer is a linear PLA-b-Dextran (PLA-b-Dex) diblock copolymer.

In some embodiments, the hydrophobic portion is a polymer comprising 2 or more repeat units. The hydrophilic portion may comprise, for example, from 2 to 200,000 repeat units depending on the size of the hydrophobic portion desired.

In some embodiments, the molecular weight of the hydrophobic portion is in the range of about 100 g/mol to about 2,000,000 g/mol, about 500 g/mol to about 200,000 g/mol, or about 1,000 g/mol to about 100,000 g/mol. The unit "g/mol" in this case refers to the weight of the hydrophobic portion per mol of the macromolecule prior to conjugation.

In some embodiments, the molecular weight of the hydrophobic portion is about 0.1 kDa to about 2000 kDa, about 0.5 kDa to about 1000 kDa, about 1 kDa to about 500 kDa, or about 1 kDa to about 100 kDa. These values represent ranges prior to conjugation.

In some embodiments, the hydrophilic portion is a polymer comprising 2 or more repeat units. The hydrophilic portion may comprise, for example, 2 to 100,000 repeat units depending on desired size of the nanoparticle.

In some embodiments, the molecular weight of the hydrophilic portion ranges from about 100 g/mol to about 1,000,000 g/mol, about 500 g/mol to 100,000 g/mol, about 1,000 g/mol to about 50,000 g/mol. The unit "g/mol" in this case refers to the weight of the hydrophilic portion per mol of the macromolecule prior to conjugation with a targeting moiety.

In some embodiments, the molecular weight of the hydrophilic portion ranges from about 0.1 kDa to about 1,000 kDa, about 0.5 kDa to 500 kDa, about 1 kDa to about 500 kDa, or about 1 kDa to 50 kDa. These values represent ranges prior to conjugation.

The relative amount of hydrophobic polymer to hydrophilic polymer in the macromolecule may be any suitable ratio that provides the desired characteristics of the resulting nanoparticle. In some embodiments, the molecular weight of the hydrophobic portion is larger than the molecular weight of the hydrophilic portion. In some embodiments, the molecular weight of the hydrophilic portion is larger than the molecular weight of the hydrophobic portion.

In some embodiments, the ratio of the molecular weight of the hydrophobic portion to the hydrophilic portion (hydrophobic portion:hydrophilic portion) is a about 0.1:1 to 100:1, about 0.5:1 to about 50:1, about 1:1 to about 10:1, about 1:1 to about 5:1, about 1:1 to about 4:1, about 1:1 to about 3:1, or about 1:1 to about 2:1. In some embodiments, the molecular weight ratio is about 5:1, 4:1, 3:1, 2:1, 1:1, 1:2, 1:3, 1:4 or 1:5. These values represent ratios before conjugation of the targeting moiety. A skilled person will be able to determine a suitable ratio based on the particular polymers selected and the agent of interest to be encapsulated.

The hydrophilic portion generally comprises a polymer having multiple reactive functional groups capable of being coupled to a targeting moiety. For example, the polymer may comprise a backbone made up of multiple monomer units, each monomer unit having multiple functional groups available for conjugation to a targeting moiety. The functional groups may, for example, be OH groups. For example, a sugar moiety in a dextran polymer may have up to 4 OH groups available for conjugation to a targeting moiety. The size of the nanoparticles and the surface density of the targeting moieties can be tuned without substantially compromising the stability of the particles, as previously described.

Thus, the hydrophilic shell of the nanoparticle provides a surface that can be functionalized, for example, by coating the nanoparticle with a desired surface density of a mucosal targeting moiety.

The proportion of functional moieties conjugated to a targeting moiety can be controlled to effect targeting. In some embodiments, at least 10%, 20%, 30%, 40%, 50%, 60%, 70%, 80%, 90%, 95%, 98%, 99% or 100% of the functional moieties on the surface of the nanoparticle are conjugated to a targeting moiety.

The targeting moiety may be a mucosal targeting moiety. As used herein, a "mucosal targeting moiety" is a targeting moiety capable of binding to a target expressed at the mucosal site. In some embodiments, the nanoparticles may comprise more than one type of mucosal targeting moiety. For example, an individual macromolecule may be functionalized with two or more different targeting moieties, or the nanoparticle may be formed from two or more macromolecules, each being functionalized with a different targeting moiety. The copolymer may optionally be functionalized, for example, on the dextran backbone of the hydrophilic portion, with one or more targeting moieties, such as a mucosal targeting moiety. In some embodiments, the mucosal targeting moiety is a phenylboronic acid (PBA) derivative.

In some embodiments, the functionalized diblock copolymer is PLA-b-Dex-g-PBA.

The nanoparticles may have a substantially spherical shape (i.e., the particles generally appear to be spherical). Such nanoparticles may also be referred to as "nanospheres" or "nanovesicles" due to their generally spherical shape and the formation of a cavity within the nanoparticle. It will be understood that the particles, for example, upon swelling or shrinkage, may adopt a non-spherical configuration.

The nanoparticles have an average particle size of less than about 1000 nm (1 micrometer). In some embodiments, the average particle size is less than about 500 nm, less than about 300 nm, less than about 200 nm, less than about 150 nm, less than about 100 nm, less than about 50 nm, less than about 30 nm, less than about 10 nm, less than about 3 nm, or less than about 1 nm in some cases. In some cases, particles less than 100 nm are preferred, for example, such particles are better able to penetrate the tear layer of the eye compared to larger particles.

In some embodiments, the average particle size is between about 0.1 nm and about 1000 nm, about 1 nm and about 500 nm, about 1 nm and about 300 nm, about 1 nm and about 200 nm, about 1 nm and about 150 nm, about 1 nm and about 100 nm, about 1 nm and about 50 nm, about 10 nm and about 150 nm, about 10 nm and about 100 nm, about 10 nm and about 75 nm, about 10 nm and about 60 nm, about 10 nm and about 50 nm, about 10 nm and about 40 nm, or about 20 and about 40 nm.

As used herein, "particle size" refers to the average characteristic dimension of a population of nanoparticles formed, where the characteristic dimension of a particle is the diameter of a perfect sphere having the same volume as the particle. A population of nanoparticles may, for example, include at least 20 particles, at least 50 particles, at least 100 particles, at least 300 particles, at least 1,000 particles, at least 3,000 particles, at least 5,000 particles, at least 10,000 particles, or at least 50,000 particles. Various embodiments of the present invention are directed to such populations of particles.

In some embodiments, the particles may each be substantially the same shape and/or size, in which case the population is substantially "monodisperse". For example, the particles may have a distribution of particle sizes such that no more than about 5% or about 10% of the particles have a particle size greater than about 10% greater than the average particle size of the particles, and in some cases, such that no more than about 8%, about 5%, about 3%, about 1%, about 0.3%, about 0.1%, about 0.03%, or about 0.01% have a particle size greater than about 10% greater than the average particle size of the particles. In some cases, no more than about 5% of the particles have a particle size greater than about 5%, about 3%, about 1%, about 0.3%, about 0.1%, about 0.03%, or about 0.01% greater than the average particle size of the particles.

The nanoparticles described herein are highly tunable. For example, the size of the nanoparticles can be tuned by adjusting the molecular weight and/or composition of the hydrophobic portion and/or the hydrophilic portion. The particular targeting moiety selected, as well as the surface density of the targeting moiety on the surface of the nanoparticles, will also impact the particle size. By adjusting the surface density of the targeting moiety, the extent of targeting can also be controlled. A high surface density of the targeting moiety can be achieved with the nanoparticles disclosed herein due to the presence of multiple functional moieties on the hydrophilic portion. Advantageously, a skilled person will be able to control the extent of targeting without substantially compromising the stability of the nanoparticle delivery system.

In some embodiments, a majority (e.g. at least 50%, 60%, 70%, 80%, 90%, 95%, 98%, 99%, or 100%) of the mucosal targeting moieties are located on the surface of the nanoparticle. It is understood that, in some cases, a portion of the mucosal targeting moieties may be located within the core of the nanoparticle when the nanoparticle forms, depending on the components of the nanoparticle and the method utilized. In some embodiments, substantially all (e.g. at least 95%, 96%, 97%, 98%, 99%, or 100%) of the mucosal targeting moieties are located on the surface of the nanoparticle. Localizing substantially all of the targeting moieties to the surface of the nanoparticles may enhance targeting efficiency.

In some embodiments, the surface density of the targeting moiety is about 1 per $nm^2$ to 15 per $nm^2$, about 1 per $nm^2$ to 10 per $nm^2$, about 1 per $nm^2$ to 5 per $nm^2$, about 1 per $nm^2$ to about 15 per $nm^2$, about 3 per $nm^2$ to about 12 per $nm^2$, or from about 5 per $nm^2$ to about 10 per $nm^2$. In some embodiments, the surface density of the targeting moiety is about 1, 2, 3, 4, 5, 6, 7, 8, 8, 9, 11, 12, 13, 14 or 15 per $nm^2$.

In some embodiments, the surface of the nanoparticle is functionalized with PBA and the density of PBA is tunable by the amount of PBA derivative in the reaction in order to control the mucoadhesion properties of the nanoparticles. The optimal density of surface functional groups may be determined by those skilled in the art in order to achieve balance between the extent of mucoadhesion and the colloidal stability of the nanoparticles.

In some embodiments, the nanoparticles are in an aqueous suspension. As used herein, a "suspension" refers to a two-phase system with substantially uniform dispersion of finely divided particles in a continuous phase of solid, liquid or gas in which the particles have minimum solubility. The finely divided particles may be referred to as the dispersed phase or external phase or discontinuous phase and the phase in which they are dispersed may be referred to as the dispersion medium or internal phase or continuous phase. In some embodiments, the nanoparticles are dispersed in aqueous medium. The aqueous medium may, for example, be a physiologically compatible aqueous medium.

The nanoparticles disclosed herein are capable of delivering an immunosuppressant to a mucosal site. The targeting moiety on the surface of the particles allows the particles to be retained at the mucosal site, thereby increasing retention time at the site. Furthermore, the nanoparticles demonstrate sustained release of immunosuppressant. The combination of retention of the nanoparticles at the target site and sustained release of immunosuppressant from the nanoparticles means that immunosuppressant is present at the mucosal site for an extended period following administration.

In some embodiments, at least a portion (e.g. at least 5%, 10%, 15% or more) of the nanoparticles are retained at the mucosal site for at least 5, 6, 7, 10, 15, 24, 36, 48, 60, 72, 84, of 96 hours. In some embodiments, at least a portion of the nanoparticles are retained at the mucosal site for a period of at least 1, 2, 3, 4 or 5 days.

In some embodiments, the immunosuppressant is released from the nanoparticle for a sustained period of at least 5, 6, 7, 10, 15, 24, 36, 48, 60, 72, 84, or 96 hours. In some embodiments, the payload is released from the nanoparticle over a period of at least 1, 2, 3, 4, 5, 6, 7 or 8 days. In some embodiments, the immunosuppressant is released from the nanoparticle over a period of at least 1 week.

The nanoparticles described herein have good loading capacity and efficiency. In some embodiments, the nanoparticles are loaded with immunosuppressant in the range of about 1 to about 40%, about 1 to about 30%, about 1 to about 20%, about 1 to about 10%, about 1% to about 8%, about 1% to about 6%, about 1% to about 5%, about 1% to about 3%, or about 1% to about 2%, about 10 to about 40%, about 10 to about 30%, or about 20% to about 30%. The loading capacity (%) is calculated here as the molecular weight of encapsulated drug over the entire weight of the nanoparticle multiplied by 100. The total weight of the nanoparticle refers to the weight of the nanoparticle including the targeting moiety and the encapsulated drug.

In some embodiments, the nanoparticles are loaded with immunosuppressant up to about 40%, up to about 30%, up to about 20%, up to about 10%, up to about 8%, up to about 6%, up to about 5%, up to about 3%, up to about 2%, or up to about 1%.

In some embodiments, the immunosuppressant agent is a hydrophobic immunosuppressant agent.

In some embodiments, the immunosuppressant agent is cyclosporine or a derivative thereof. Cyclosporines are a class of peptide compounds having various pharmaceutical applications, such as immunosuppressant and anti-inflammatory applications. Cyclosporines include cyclosporine A, B7 C and D. The most widely investigated cyclosporine is cyclosporine A and cyclosporine A derivatives. Various cyclosporine derivatives have been described in the literature, for example, U.S. Pat. No. 4,649,047, U.S. Pat. No. 6,254,860, U.S. Pat. No. 6,350,442, US 2010/006117, each of which is incorporated herein by reference. In some embodiments, the immunosuppressant is cyclosporine A.

The immunosuppressant may be loaded into any embodiment of nanoparticle described herein. The mucoadhesive nanoparticle compositions may be prepared and loaded with immunosuppressant according to any suitable method known in the art, including and those described previously by the present inventors (Verma et al. 2012; Liu et al. 2012). In some embodiments, the mucoadhesive nanoparticle compositions are prepared according to the methods described herein in the examples.

Pharmaceutical compositions for administering an immunosuppressant to a mucosal site can be prepared in any manner known in the pharmaceutical arts. In one embodiment, the pharmaceutical composition comprises a mucoadhesive nanoparticle composition as described in any embodiment disclosed herein; an immunosuppressant; and one or more pharmaceutically acceptable carriers, diluents or excipients. The pharmaceutical compositions are suitable for topical administration to a mucosal site. Non-limiting examples of dosage forms suitable for topical or administration include ointments, pastes, creams, lotions, gels, powders, solutions, suspensions, emulsions, sprays, inhalants, or patches. The composition is typically admixed under sterile conditions with a pharmaceutically acceptable carrier and any needed preservatives or buffers as may be required. In some embodiments, the pharmaceutical composition is a suspension. In some embodiments, the pharmaceutical composition is an aqueous suspension for topical administration to an anterior surface of the eye. In some embodiments, the dosage form is a drop, gel or ointment. In some embodiments, the dosage form is an eye drop formulation. In some embodiments, the formulation is sterile. In some embodiments, the formulation is isotonic. In some embodiments, the preservative may include a cryoprotectant. In some embodiments, the cryoprotectant may be trehalose.

In some embodiments, the concentration of immunosuppressant in the pharmaceutical composition is about 0.001% to about 0.1%, about 0.01 to about 0.1%, about 0.01% to about 0.05%. Where the composition is a liquid, the unit is % wt/vol. Where the composition is a solid, the unit is % wt/wt. In some embodiments, the composition is a liquid formulation, such as an ophthalmic formulation, comprising about 0.001% to about 0.1% wt/vol, about 0.01 to about 0.1% wt/vol, about 0.01% to about 0.05% wt/vol of immunosuppressant.

As noted above, in some embodiments, the immunosuppressant is cyclosporine A. Restasis® is a commercially-available ophthalmic formulation comprising 0.05% wt/vol CsA for treatment of dry eye syndrome. In this formulation, CsA is administered as a 28 µL drop containing 14 µg CsA at an administration frequency of 2 drops per day for each eye to be treated. This results in an overall dose of about 28 µg CsA per day or about 196 µg CsA per week. This dosage regime is known to have negative side effects such as patient discomfort and damage to the ocular surface.

The function and integrity of a mucosal lining can be sensitive to the concentration and administration frequency of immunosuppressant applied thereto. High doses and/or frequent administration can negatively impact the integrity and function of a mucosal lining. Furthermore, chronic inflammation and/or dryness can also negatively impact the integrity and/or function of mucosal linings. The "integrity" of a mucosal lining includes a healthy epithelial layer and healthy goblet cells, and the "function" of a mucosal lining includes the production of mucins and hydration of the mucosal lining.

The present inventors surprisingly discovered that, by administering CsA via mucoadhesive nanoparticles of the present disclosure, a therapeutic effect of CsA could be achieved at a significantly reduced dose and/or administration frequency compared to Restasis®. Advantageously, at a low overall dose (e.g. less than 5% compared to Restasis®), a therapeutic effect could be achieved with reduced negative side effects compared to Restasis®. For example, it was demonstrated that at overall doses less than 5% (e.g. less than 5, 4, 3, 2 or 1%) compared to Restasis®, a therapeutic effect could be achieved while preserving the integrity and function of the mucosal lining. Furthermore, it was demonstrated that at overall doses less than 5% (e.g. less than 5, 4, 3, 2 or 1%) compared to Restasis®, a therapeutic effect could be achieved while also promoting recovery of a damaged mucosal lining. Administration of mucoadhesive nanoparticles (even empty nanoparticles) according to the present disclosure was also surprisingly found to improve hydration of the mucosal lining in an experimental model of dry eye syndrome. Thus, the nanoparticles themselves may have a soothing effect.

The compositions disclosed herein may be administered at any suitable dosage and/or administration frequency that provides a therapeutic effect and is tolerable to the patient. In some embodiments, the composition is administered at a dosage and/or frequency that provides a therapeutic effect while preserving or restoring the integrity and/or function of the mucosal lining. In some embodiments, the integrity and/or function of the mucosal lining is substantially preserved or restored up to about 100% compared to normal (or baseline), at least 90% compared to normal, at least 80% compared to normal, at least 70% compared to normal, about 50% compared to normal, or about 50% compared to normal. In some embodiments, the integrity and/or function of the mucosal lining is preserved or restored e.g. to at least 90%, 95%, 99% or 100% compared to normal (or baseline). Mucosal integrity and function may be assessed by any method know in the art. For example, the ocular mucosa may be assessed by performing impression cytology on the ocular surface. This procedure removes the superficial lining of the ocular surface epithelium. The epithelium and goblet cells can then be assessed, for example, by histological analysis.

In some embodiments, the composition is administered at a dosage and/or frequency that promotes hydration of the mucosal lining.

In some embodiments, the CsA is administered at an overall dose less than about 10% that of Restasis® while still achieving a therapeutic effect. In some embodiments, the CsA is administered at an overall dose less than about 7.5% that of Restasis®, less than about 5% that of Restasis®, less than about 4% that of Restasis®, less than about 3% that of Restasis®, less than about 2% that of Restasis®, less than about 1% that of Restasis®.

As used herein, "overall dose" means the total dose of immunosuppressant per unit of time. In a given unit of time, the immunosuppressant may be administered in a single dose or it may be divided over multiple doses. For example, the overall dose may be a weekly dose divided into 2, 3, 4, 5, 6, 7, 8, 9, 10, 11, 12, 13, 14 individual doses. It will also be understood that a dose refers to a dose per area to be treated, e.g. a dose per eye.

In some embodiments, CsA is administered at a dose of less than about 20 µg per day, less than about 15 ug per day, less than about 14 ug per day, less than about 13 ug/day, less than about 12 ug per day, less than about 11 ug/day, less than about 10 µg per day, less than about 5.0 µg per day, or less than 1 µg/day, less than 0.5 µg/day, less than 0.3 µg/day, or less than about 0.1 ug/day. In embodiments where cyclosporine A is not administered every day, it will be understood that the daily dose as an average dose per day (e.g. 7 µg per week=average of 1 µg per day). In some embodiments, cyclosporine A is administered at a daily dose or an average dose of about 1, 2, 3, 4, 5, 6, 7, 8, 9, 10, 11, 12, 13, 14, 15, 16, 17, 18, 19 or 20 µg/day.

In some embodiments, CsA is administered at a dose of about 0.1 µg to about 150.0 µg per week, about 0.1 µg to about 125.0 µg per week, about 0.1 µg to about 100.0 µg per week, about 0.1 µg to about 75.0 µg per week, about 0.1 µg to about 50.0 µg per week, about 0.1 to about 20.0 µg per week, about 0.1 to about 10.0 µg/week, about 0.1 to about 5.0 µg/week. In some embodiments, CsA is administered at a dose of about 1.0 to about 100.0 µg/week, about 1.0 to about 75.0 µg/week, about 1.0 µg to about 50.0 µg per week about 1.0 to about 40.0 µg/week, about 1.0 to about 30.0 µg/week, about 1.0 to about 20.0 µg/week, about 1.0 to about 10.0 µg/week, about 1.0 to about 7.5 µg/week, about 1.0 to about 5.0 µg/week, about 1.0 to about 3.0 µg/week, about or about 1.0 to about 2.0 µg/week. In some embodiments, CsA is administered at a dose of less than about 150 ug/week, less than about 125 ug/week less than about 100 ug/week, less than about 75 ug/week, less than about 50 ug/week, less than about 25 ug/week, less than about 20 ug/week, less than about 15 ug/week, less than about 10 ug/week, less than about 5 ug/week, less than about 3 ug/week. In some embodiments, cyclosporine A is administered at a dose of about 1, 2, 3, 4, 5, 6, 7, 8, 9, 10, 11, 12, 13, 14, 15, 16, 17, 18, 19, 20, 30, 40, 50, 75 or 100 µg/week.

In some embodiments, the pharmaceutical composition is administered twice a day, once a day, once every 2 days, once every 3 days, once every 4 days, once every 5 days, once a week, once every two weeks, or once a month. Preferably, the composition is administered less than twice per day. In some embodiments, the composition is administered less than 10, 9, 8, 7, 6, 5, 4, 3 or 2 times per week. In some embodiments, the composition is administered once a week. In some embodiments, the composition is administered once every 1, 2, 3, 4, 5, 6, 7, 8, 9, 10, 11, 12, 13, 14, 15, 16, 17, 18, 19 or 20 days. In some embodiments, the composition is administered once a day.

In some embodiments, the immunosuppressant is administered at the same dose or dosage for as long as needed. In other embodiments, the immunosuppressant is administered at more than one different dose. For example, the immunosuppressant may be administered at a first dose for a first period of time and may, subsequently, be administered at a second dose for a second period of time. In some embodiments, the second dose is higher than the first dose. In some embodiments, the second dose is lower than the first dose. In some embodiments, the first and second time period are the same. In some embodiments, the second time period is shorter than the first time period. In some embodiments, the second time period is longer than the first time period. For example, in some embodiments, the immunosuppressant may be administered at a low dose at first to gauge tolerability and/or efficacy. The dose may then be adjusted up or down depending on the outcome. In one embodiment, the immunosuppressant is administered at a first overall dose of 1 to 100 ug per week (e.g. 1, 2, 3, 4, 5, 6, 7, 8, 9 or 10) for a first time period of 1 or 2 weeks. If tolerability is good or efficacy is unsatisfactory, the dose may be increased, for example, by about 5, 10, 15, 20, 25, 50, 75, 100, 150, 200, 150 or 300%. The first or second dose may be maintained for any suitable time period. It will be understood that there may be more than two doses and/or time periods (e.g. 3, 4, 5, 6, 7, 8, 9 or 10). Furthermore, it will be understood that if the dose represents an overall dose, the dose may be split into multiple doses.

The compositions disclosed herein show good tolerability and are suitable for acute (short term) or chronic (long term) use. As used herein, "acute" use refers to periodic use or short term use (e.g. less than 2 weeks), for example, to treat an acute immune (e.g. allergic) reaction. As used herein, "chronic" use refers to regular use over a longer period of time, for example, to treat a chronic disease or condition of the eye, such as dry eye syndrome. It has been discovered that, in some embodiments, the compositions disclosed herein are capable of being administered at a dose and/or frequency that provides a therapeutic effect while preserving or restoring the function and/or integrity of the mucosal lining. In a chronic model of dry eye syndrome in mice, it was surprisingly discovered that a weekly dose less than 3% that of a Restasis® group provided a therapeutic effect with little to no damage to the mucosal surface evident at the end of the study. The doses that achieved this surprising effect (0.3/0.6 µg/week) were less than half of the dose of CsA previously reported using the mucoadhesive nanoparticles described herein, which was about 1.5 µg/week in an acute study (38). In the chronic study reported herein, both the Restasis® group and the nanoparticle group receiving a higher dose of CsA (1.5 µg/week) showed signs of mucosal damage following chronic treatment. Advantageously, the administration frequency in all of the nanoparticle groups was less than 5% that of the Restasis® group since the composition was administered once per week rather than 21 times per week (3×day). The optimal combination of dose and/or frequency to achieve the desired effect may be determined by persons of skill in the art.

The pharmaceutical compositions disclosed herein are useful in the treatment of diseases and conditions capable of being treated via administration of an immunosuppressant to a mucosal site. In some embodiments, the disease or condition to be treated is a disease or condition involving inflammation (e.g. excessive immune activity). As used herein, the expression "involving inflammation" is meant to indicate that inflammation is a characteristic or symptom of the disease or condition and that benefit can be obtained by reducing the inflammation, e.g. reducing excessive immune activity. The inflammation may be in the mucosal lining, in the underlying tissue, at a nearby site, or in any location that the immunosuppressant is capable of reaching following administration to the mucosal site In some embodiments, the mucosal site is a mucosal site of the eye, ear, nose, mouth, esophagus, stomach, small intestine, large intestine, rectum, vagina, urethra, penis or uterus.

In some embodiments, the disease or condition to be treated is a disease or condition of the eye. Non-limiting examples include dry eye syndrome (keratoconjunctivitis sicca), abrasion, acanthamoeba keratitis, actinic keratosis, acute allergic blepharoconjunctivitis, allergic conjunctivitis, adenoviral keratoconjunctivitis, aniridia, atopic keratoconjunctivitis, bacterial conjunctivitis, bacterial keratitis, band keratopathy, basal cell carcinoma, blepharitis, bullous keratopathy, canaliculitis, caruncular cyst, cataract, chalazion, chlamydial conjunctivitis, climatic droplet keratopathy, concretions, conjunctival intraepithelial neoplasia, conjunctival lymphoma, conjunctival papilloma, conjunctival pigmented lesions, conjunctival scarring, conjunctivitis, conjunctivochalasia and chemosis, corneal collagen cross-linking, corneal edema, corneal graft—lamellar keratoplasty, corneal graft rejection, corneal infiltrates, crocodile shagreen, crystalline keratopathy, cysts of the eye lids, dacryocystitis, dellen, dendritic ulcer, dermatochalasis and blepharochalasis, Descemet's membrane breaks, disciform keratitis, disciform keratitis, ectopia lentis, ectropion, endophthalmitis, entropion, epiblepharon and epicanthic folds, epibulbar choristomas, epiphora, episcleritis, epithelial and fibrous ingrowth, epithelial basement membrane dystrophy, exposure keratopathy, eyelid trauma, filamentary keratopathy, filtering bleb, flash burns, floppy eyelid syndrome, follicular conjunctivitis, Fuchs' endothelial dystrophy, Fuchs' heterochromic iridocyclitis, fungal keratitis, giant papillary conjunctivitis, glaucoma—acute angle closure, gonococcal keratoconjunctivitis, granular dystrophy, hemangioma, herpes simplex keratitis, herpes simplex primary blepharokeratoconjunctivitis, herpes zoster ophthalmicus, hordeolum—internal and external, hyphema—blunt trauma, hypopyon, infectious crystalline keratopathy, interstitial keratitis, iridocorneal dysgenesis, iridocorneal endotheliopathy, iris cysts, iritis, iron lines, keratoconus, keratoconus forme frusta, keratoglobus, lattice stromal dystrophy, leukocoria, lice, limbal stem cell deficiency, lipid keratopathy, macular stromal dystrophy, marginal keratitis, meesmann's dystrophy, melanoma—conjunctival and eyelid, melanoma and nevus of the iris, membranous and pseudomembranous conjunctivitis, molluscum contagiosum, mooren's ulcer, nasolacrimal duct obstruction—congenital, neurotrophic keratopathy, nevus—eyelid, ocular cicatricial pemphigold, ophthalmia neonatorum, pannus and pseudopterygia, pellucid marginal degeneration, perforation—corneal, peripheral ulcerative keratitis, persistent epithelial defect, phlyctenulosis, pingueculum, posterior capsular opacification, posterior polymorphous dystrophy, preseptal cellulitis, pseudoexfoliation of the lens capsule, pterygium, ptosis and pseudoptosis, punctual stenosis, pyogenic granuloma, recurrent corneal erosion syndrome, Reis-Buckler's dystrophy, retention cyst and lymphangiectasia, rheumatoid arthritis, rosacea keratitis, Salzmann nodular degeneration, scleritis, sebaceous cell carcinoma, seborrheic keratosis, squamous cell carcinoma—lid, Stevens-Johnson syndrome, sub-conjunctival hemorrhage, superficial punctate keratopathy, superior limbic keratoconjunctivitis, synechia, Terrien's marginal degeneration, Thygeson's superficial punctate keratopathy, toxic keratopathy, trachoma, trichiasis, pseudotrichiasis, distachiasis, metaplastic lashes, trichotillomania, uveitis, vernal keratoconjunctivitis, vortex keratopathy, xanthelasma.

In some embodiments, the disease or condition to be treated is dry eye syndrome. As used herein, "dry eye syndrome" (DES), also known as keratoconjunctivitis sicca, refers to a multifactorial disease affecting the tear film and the ocular surface that results in symptoms of discomfort, dryness, inflammation, visual disturbance, and tear film instability with potential damage to the ocular surface. The phrase "keratoconjunctivitis sicca" is Latin, and its translation is "dry [inflammation] of the cornea and conjunctiva". DES can develop in the absence of any other overt system abnormality or may be associated with a systemic disease.

In some embodiments, the composition is administered topically on the surface of the eye for treatment of a disease or condition associated with the anterior of the eye. In some embodiments, the composition is administered topically on the surface of the eye for treatment of a disease or condition associated with the posterior of the eye. In some embodiments, the composition is administered topically on the surface of the eye for treatment of a disease or condition associated with the interior of the eye.

As used herein "treating" includes preventing, reducing or alleviating one or more signs and/or symptoms of the disease or condition. For example, in the treatment of dry eye syndrome, treatment may result in one or more of reduced inflammation, increased comfort and improved hydration of the mucosal surface. As used herein, "increased comfort" means a perceived increase in eye comfort by the patient, which could mean a reduction or elimination of a negative sensation, such as pain, stinging, itching and/or dryness. In some embodiments, the composition is administered at dosage and/or administration frequency that is capable of providing a therapeutic effect (e.g. one or more of reduced inflammation, increased comfort and improved hydration of the mucosal lining) while preserving the integrity and/or function of the mucosal lining.

In some embodiments, there is provided a method for the treatment of a disease or condition involving inflammation comprising topically administering to a mucosal surface of a subject a pharmaceutical composition comprising nanoparticles capable of releasing an immunosuppressant at the mucosal site, the nanoparticles comprising a plurality of linear amphiphilic block copolymers including a hydrophilic block and a hydrophobic block, the hydrophobic block comprising polylactide (PLA) and the hydrophilic block comprising dextran (Dex), the nanoparticles being functionalized with a mucosal targeting moiety. In some embodiments, the mucosal surface is an ocular surface of an eye. The composition may be a composition is a composition described in any embodiment disclosed herein.

In some embodiments, there is provided a method for reducing inflammation on a surface of an eye, comprising topically administering to a mucosal surface of the eye a pharmaceutical composition comprising nanoparticles, the nanoparticles comprising a plurality of linear amphiphilic block copolymers each including a hydrophilic block and a hydrophobic block, the hydrophilic block comprising dextran (Dex) and the hydrophobic block comprising polylactide (PLA), the nanoparticles being functionalized with a mucosal targeting moiety.

In some embodiments, there is provided a method for treating dry eye syndrome, comprising topically administering to a mucosal surface of the eye a pharmaceutical composition comprising nanoparticles, the nanoparticles comprising a plurality of linear amphiphilic block copolymers each including a hydrophilic block and a hydrophobic block, the hydrophilic block comprising dextran (Dex) and the hydrophobic block comprising polylactide (PLA), the nanoparticles being functionalized with a mucosal targeting moiety.

In some embodiments, there is provided a method for hydrating a mucosal surface comprising topically administering to the mucosal surface a pharmaceutical composition comprising nanoparticles, the nanoparticles comprising a plurality of linear amphiphilic block copolymers each including a hydrophilic block and a hydrophobic block, the hydrophilic block comprising dextran (Dex) and the hydrophobic block comprising polylactide (PLA), the nanoparticles being functionalized with a mucosal targeting moiety. In some embodiment, the composition further comprises an immunosuppressant. In some embodiments, the mucosal surface is an ocular surface of an eye and the pharmaceutical composition is a composition described in any embodiment disclosed herein.

In other embodiments, there are provided "uses" of the compositions or components thereof as defined herein for treating a disease or condition. In other embodiments, there are provided uses of the compositions or components thereof as defined herein for the manufacture of a medicament for treating a disease or condition.

The compositions described herein may be formulated in unit dosage form for ease of administration and uniformity of dosage. The expression "unit dosage form" as used herein refers to a physically discrete unit appropriate for the patient to be treated. It will be understood, however, that the dose and administration schedule may be optimized for a particular patient, for example, by a prescribing physician. For any composition, the therapeutically effective dose can be estimated initially either in cell culture assays or in animal models, usually mice, rabbits, dogs, or pigs. The animal model is also used to achieve a desirable concentration range and route of administration. Such information can then be used to determine useful doses and routes for administration in humans. Therapeutic efficacy and toxicity can be determined by standard pharmaceutical procedures in cell cultures or experimental animals, e.g., ED50 (the dose is therapeutically effective in 50% of the population) and LD50 (the dose is lethal to 50% of the population). The dose ratio of toxic to therapeutic effects is the therapeutic index, and it can be expressed as the ratio, LD50/ED50. Pharmaceutical compositions which exhibit large therapeutic indices may be useful in some embodiments. The data obtained from cell culture assays and animal studies can be used in formulating a range of dosage for human use.

The subject may be a human or non-human animal. In some embodiments, the subject is a mammal. Non-limiting examples of mammals include human, dog, cat, horse, donkey, rabbit, cow, pig, sheep, goat, rat, mouse, guinea pig, hamster, and primate. In some embodiments, the subject is a human.

As used herein, the term "about" when used in conjunction with a numerical value means +/−10%.

Embodiments

In some embodiments, there is provided pharmaceutical composition for use in treating a disease or condition capable of being treated via topical administration of an immunosuppressant to a mucosal site, the pharmaceutical composition comprising nanoparticles capable of releasing an immunosuppressant, the nanoparticles comprising a plurality of linear amphiphilic block copolymers including a hydrophilic block and a hydrophobic block, the hydrophobic block comprising polylactide (PLA) and the hydrophilic block comprising dextran (Dex), the nanoparticles being functionalized with a mucosal targeting moiety, wherein the pharmaceutical composition is administered in an effective amount capable of treating the disease or condition while substantially preserving or restoring the function and/or integrity of the mucosal lining.

In some embodiments, the amphiphilic block copolymers comprise PLA-b-Dex and wherein the mucosal targeting moiety is a derivative of phenylboronic acid (PBA), e.g. PLA-b-Dex-g-PBA. In some embodiments, the mucosal surface is a mucosal surface of the eye. In some embodiments, the disease or condition is dry eye syndrome. In some embodiments, the treating provides one or more of reduced inflammation, increased comfort or improved hydration of the mucosal lining. In some embodiments, the composition is formulated as an aqueous suspension for administration to an anterior surface of an eye. In some embodiments, the concentration of immunosuppressant in the composition is about 0.001% to about 0.1% wt/vol, about 0.01 to about 0.1% wt/vol or about 0.01% to about 0.05% wt/vol. In some embodiments, the immunosuppressant is cyclosporine or a derivative thereof, such as cyclosporine A. In some embodiments, the cyclosporine A is administered at a dose of about 0.1 µg to about 150.0 µg per week, about 0.1 µg to about 125.0 µg per week, about 0.1 µg to about 100.0 µg per week, about 0.1 µg to about 75.0 µg per week, about 0.1 µg to about 50.0 µg per week, about 0.1 to about 20.0 µg per week, about 0.1 to about 10.0 µg/week, about 0.1 to about 5.0 µg/week. In some embodiments, the composition is administered once every 1, 2, 3, 4, 5, 6, 7, 8, 9, 10, 11, 12, 13, 14, 15, 16, 17, 18, 19 or 20 days, such as once per day or once per week. In some embodiments, at least a portion of the nanoparticles are retained at the mucosal site for at least 5 hours.

In some embodiments, there is provided a topical pharmaceutical composition for use in the treatment of dry eye syndrome, the composition being an aqueous suspension for administration to the anterior surface of the eye, the composition comprising nanoparticles capable of releasing cyclosporine A, the nanoparticles comprising a plurality of linear amphiphilic block copolymers including a hydrophilic block and a hydrophobic block, the hydrophobic block comprising polylactide (PLA) and the hydrophilic block comprising dextran (Dex), the nanoparticles being functionalized with a mucosal targeting moiety, such as such as a derivative pf phenylboronic acid (PBA), wherein the composition is formulated for administration of cyclosporine A at an overall dose of less than about 150.0 µg per week at an administration frequency of less than 10 times per week, such as, once per day or once per week. In some embodiments, the composition is formulated for administration as an eye drop, wherein one drop is to be administered every 1, 2, 3, 4, 5, 6, 5, 6 or 7 days.

In some embodiments, there is provided a use of a mucoadhesive nanoparticle composition comprising cyclosporine A in the manufacture of a medicament for treating a disease or condition capable of being treated via topical administration of cyclosporine A to a mucosal site, the nanoparticles capable of releasing cyclosporine A, the nanoparticles comprising a plurality of linear amphiphilic block copolymers including a hydrophilic block and a hydrophobic block, the hydrophobic block comprising polylactide (PLA) and the hydrophilic block comprising dextran (Dex), the nanoparticles being functionalized with a mucosal targeting moiety, wherein the pharmaceutical composition is administered in an effective amount capable of treating the disease or condition while substantially preserving or restoring the function and/or integrity of the mucosal lining.

In some embodiments, there is provided a pharmaceutical composition for use in hydrating a mucosal lining, such as a mucosal lining of the eye, the composition comprising nanoparticles, the nanoparticles comprising a plurality of linear amphiphilic block copolymers including a hydrophilic block and a hydrophobic block, the hydrophobic block comprising polylactide (PLA) and the hydrophilic block comprising dextran (Dex), the nanoparticles being functionalized with a mucosal targeting moiety, such as a derivative of phenylboronic acid (PBA), the composition optionally further comprising an immunosuppressant.

All definitions, as defined and used herein, should be understood to control over dictionary definitions, definitions in documents incorporated by reference, and/or ordinary meanings of the defined terms.

The following examples are intended to illustrate certain exemplary embodiments of the present disclosure. However, the scope of the present disclosure is not limited to the following examples.

EXAMPLES

Example 1: Formulation of Cyclosporine A in Mucoadhesive Nanoparticles

Acid-terminated poly(D,L-lactide) (PLA; Mw ~20) were purchased from Lakeshore Biomaterials (Birmingham, USA) and washed with methanol to remove monomer impurities. Dextran (Dex; Mw ~10 kDa), hydrochloric acid (HCl), triethylamine (TEA), N-(3-dimethylaminopropyl)-N-ethyl carbodiimide (EDC), 3-Aminophenylboronic acid monohydrate (PBA), sodium periodate (NaIO4), glycerol, sodium cyanoborohydride (NaCNBH$_3$), and Cyclosporine A (CsA) were purchased from Sigma Aldrich (Oakville, Canada) N-Hydroxysulfosuccinimide (Sulfo-NHS) and N-Boc-ethylenediamine were purchased from CNH Technologies (Massachusetts, USA).

The conjugation of the poly(D,L-lactide) (PLA) and dextran (Dex) polymer chains to form a block copolymer PLA-b-Dex and the surface modification of the PLA-b-Dex NPs with PBA were reported previously (Verma et al., 2012; Liu et al. 2012). Briefly, the aldehyde end group of the Dex was conjugated with the N-Boc-ethylenediamine linker through reductive amination with NaCNBH$_3$. After conjugation with the linker, the Boc group was deprotected using HCl/TEA treatment. The deprotected amine end group is then conjugated with the carboxyl terminal group of the PLA using Sulfo-NHS and EDC as catalysts. The surface of these NPs were modified with PBA molecules by a two-step approach: the hydroxyl groups of the Dex were oxidized to form more reactive aldehyde groups in the presence of NaIO$_4$, and the aldehyde groups were conjugated with the amine groups of PBA molecules through reductive amination. The amount of PBA attached to the Dex chain was quantified using UV-Vis absorption at 291 nm after obtaining the standard calibration of PBA in DMSO. The PLA-b-Dex polymers in DMSO were used as the baseline.

The encapsulation of CsA in the PBA-modified NPs (PLA-b-Dex-g-PBA NPs) was performed using a nanoprecipitation method. 1 ml of DMSO containing polymer (~7 mg/ml) and CsA (varied concentration) was slowly added into 10 ml of Millipore water under mild stirring for self-assembly of NPs carrying the drugs. The NP-drug mixture was then syringe filtered (pore size=200 nm) to remove NP or drug aggregates, and dialyzed against water to remove some of the free drugs and DMSO from the mixture. The sizes of the nanoparticles were determined using dynamic light scattering (DLS) technique. The amount of CsA in the final mixture was determined using High-performance liquid chromatography (HPLC; C18 HPLC column, ACN/H$_2$O 75:25 as the mobile phase with UV-absorption detection at 210 nm).

The nanoparticles were fabricated with approximately 15.2±1.0 mol % of PBA on dextran monomer (mol of PBA/mol dextran monomers). The diameter of the raw nanoparticles was 25.4±0.6 nm. With encapsulation of CsA, the diameter increased slightly to 26.9±1.1 nm (MNP w. CsA (0.3/0.6 µg×1/wk)), and to 29.1±0.3 nm (MNP w. CsA (1.5 µg×1/wk)) (Liu et al. 2012; Liu et al. 2014). From HPLC analysis, the MNP w. CsA (1.5 µg×1/wk) group contained approximately 1.5 µg of CsA in a 7 µl eye drop (along with approximately 4 µg of the PLA-b-Dex-g-PBA NPs). This means that the MNP w. CsA (1.5 µg×1/wk) group had about the same amount of CsA in a 7 µl drop as that in a 3 µl drop of Restasis®. Due to the dosing frequency differences between Restasis® and MNP w. CsA (1.5 µg×1/wk), the overall dosage of CsA in MNP w. CsA (1.5 µg×1/wk) is approximately 5% that of Restasis® (or 1/21 that of Restasis®). Similarly, the MNP w. CsA (0.3/0.6 µg×1/wk) group had 0.3 µg of CsA in the 7 µl drop for the first two weeks of administration, and 0.6 µg for the subsequent two weeks. Thus, the dosage of MNP w. CsA (0.3/0.6 µg×1/wk) is approximately 1% that of Restasis® (or 1/105$^{th}$ of Restasis®) for the first two weeks, and 2% (2/105$^{th}$ of Restasis®) for the subsequent two weeks. The MNP w. CsA (1.5 µg×1/wk) and MNP w. CsA (0.3/0.6 µg×1/wk) showed total in vitro release for up to 4 and 5 days respectively, similar to our previous study (Liu et al. 2012).

Example 2: Dry Eye Induction in C57BL/6 Mice and Tear Volume Measurements

To evaluate the efficacy of NPs carrying CsA in treating DES, an experimental murine dry eye model was used.[39] Transdermal scopolamine patches (Transderm-V, Novartis; 1.5 mg of scopolamine) were cut into two pieces and wrapped around the midtails of the mice and secured with surgical tape. The patches were replaced every other day through the duration of the study. To simulate a desiccating environment, mice cages (open-top) were placed in a fumehood for 1 hr, 3 times a day throughout the study. After 4 days of dry eye induction, the mice were divided into 6 groups of 5 mice and the administration of various formulations were initiated (Table 1). Note that dry eye was not induced in the Healthy group and no administration was given to that group of mice. Saline, MNP w/o. CsA, MNP w. CsA (0.3/0.6 µg×1/wk) and MNP w. CsA (1.5 µg×1/wk) were administered once a week (on days 5, 12, 19 and 26), while Restasis® was given 3 times a day throughout the study period. On days 5, 12, 19 and 26, before the weekly administrations, tear production measurements were performed. On the final day (day 33), the mice were euthanized and the ocular tissues extracted for histopathology analysis.

TABLE 1

6 different groups applied to the mice for treatment of experimental dry eye.

| Treatment group | Dry eye induced | Admin. volume (µl) | NP (µg) | CsA (µg) | Admin. frequency |
|---|---|---|---|---|---|
| Healthy | No | 0 | 0 | 0 | |
| Saline | Yes | 7 | 0 | 0 | ×1/week |
| MNP w/o. CsA | Yes | 7 | 4 | 0 | ×1/week |
| MNP w. CsA (0.3/0.6 µg × 1/wk) | Yes | 7 | 4 | 0.3/0.6* | ×1/week |
| MNP w. CsA (1.5 µg × 1/wk) | Yes | 7 | 4 | 1.5 | ×1/week |
| Restasis ® | Yes | 3 | 0 | 1.5 | ×3/day |

*MNP w. CsA (0.3/0.6 µg × 1/wk) was administered with 0.3 µg of CsA for the first two weeks, and with 0.6 µg of CsA for the subsequent two weeks.

Tear production was measured by holding a phenol red thread (Zone-quick; White Ophthalmic Supply, Canada) with jeweler's forceps in the lateral canthus of the ocular surface for 30 seconds. The length of the dyed segment (red) of the thread was measured and recorded.

Figure 2:
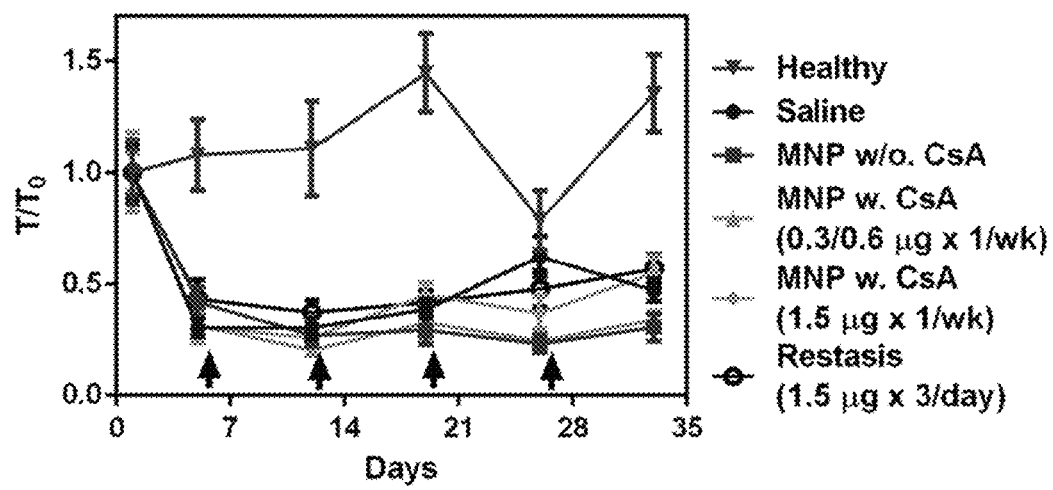
FIG. 2. Tear production measurement of dry eye induced mice treated with various formulations. The tear volumes (T) were normalized with respect to their initial tear volume ($T_0$). Note that dry eye was not induced in Healthy group. The arrows represent the weekly dosing regimen of Saline, MNP w/o. CsA, MNP w. CsA (0.3/0.6 μg×1/wk) and MNP w. CsA (1.5 μg×1/wk) groups. Restasis (1.5 μg×3/day) was administered three times a day. MNP w. CsA (0.3/0.6 μg×1/wk) was administered with 0.3 μg of CsA per week for the first two weeks, and with 0.6 μg of CsA per week for the subsequent two weeks.

All the groups (with the exception of the Healthy group) underwent dry eye induction, which was reflected in the sudden drop of tear production after 4 days (ie, on day 5) (FIG. 2). The Healthy group maintained a relatively stable tear production throughout the study except on week 3 (day 26). This slight drop in tear production is also reflected on the reduced corneal fluorescein clearance (FIG. 3, top row) observed on day 26, while on all the other measurement time points the fluorescein was rapidly cleared from the corneal surface within 10 minutes. The tear production for all the treatment groups remained at or below half of the initial tear production rate throughout the duration of the study. Only the MNP w. CsA (1.5 µg×1/wk) group was able to significantly increase its tear production at the end of the study (day 33) compared to before the start of weekly administrations (day 5) (p<0.05), but it was only able to restore up to about 50% of the initial tear production rate (day 1). It should be noted that tear production rate is not the primary indicator of dry eye treatment in this study since the mice were constantly exposed to dry conditions and anticholinergic administrations to simulate the experimental dry eye disease. The main indicator of dry eye treatment in this study using immunosuppressant agent, CsA, is the elimination of ocular inflammation. Inflammation of ocular tissues such as lacrimal glands has been identified as one of the primary sources of reduced tear secretion in dry eye syndrome, and the treatment of this inflammation using CsA formulations has been shown to improve the rate of tear secretion over time (Pflugfelder, 2004).

Figure 3:
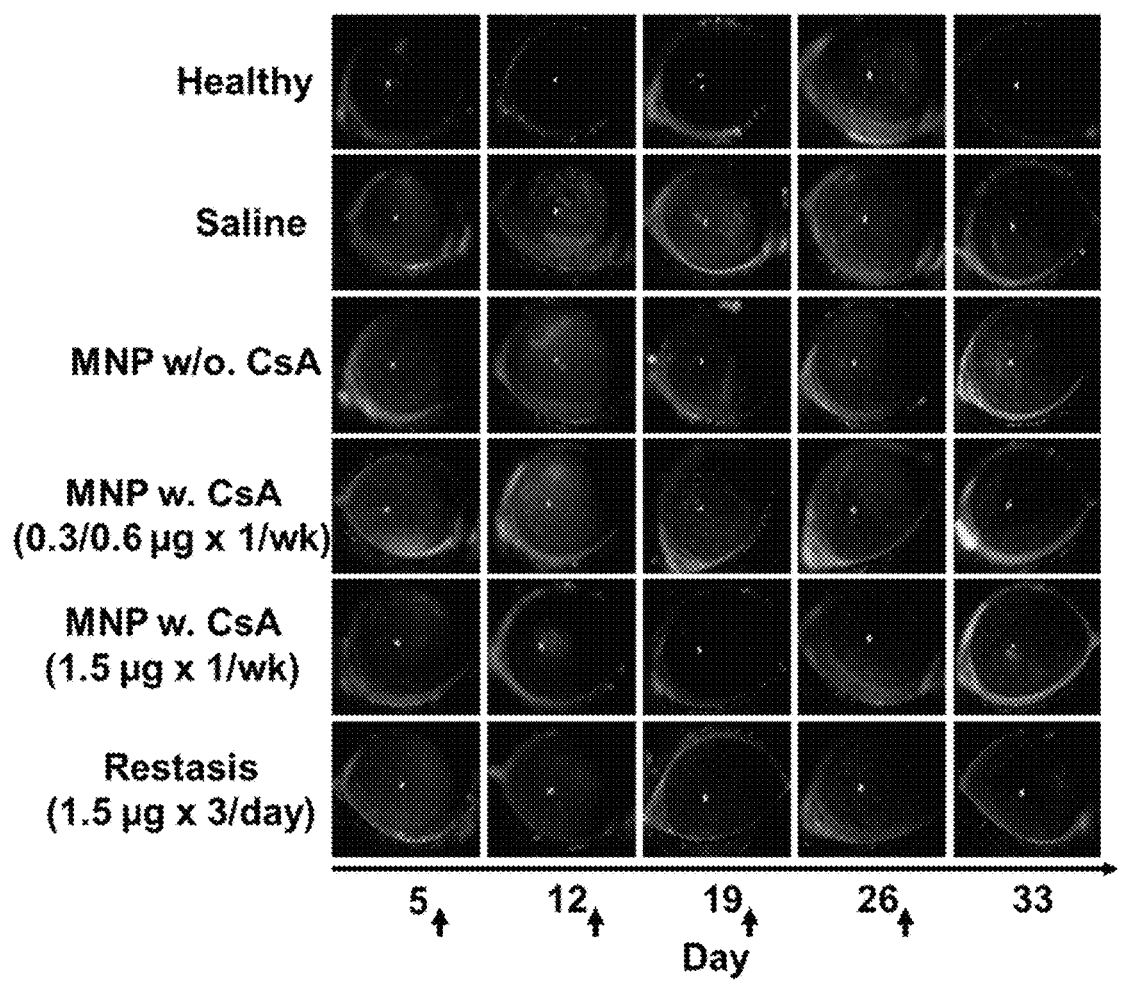
FIG. 3. Corneal fluorescein staining analysis of mice with different treatment groups. The arrows represent weekly dosing regimen of Saline, MNP w/o. CsA (1/wk), MNP w. CsA (0.3/0.6 μg×1/wk) and MNP w. CsA (1.5 μg×1/wk) groups. Restasis (1.5 μg×3/day) was administered three times a day. Note that the analysis does not take into account the fluorescein on the lid margins of the eyes. MNP w. CsA (0.3/0.6 μg×1/wk) was administered with 0.3 μg of CsA per week for the first two weeks, and with 0.6 μg of CsA per week for the subsequent two weeks.

The dry eye induction was confirmed by the drastic drop in tear production rate within 4 days (FIG. 2), as well as the increased amount of fluorescein staining on the corneal surface (day 5) compared to the Healthy control group (FIG. 3). From both tear production measurements and fluorescein staining analysis, most of the mice in the groups after dry eye induction (excluding the Healthy group) maintained the dry eye conditions throughout the study (from day 5 to day 33) without much improvement in these clinical parameters. The only groups that showed statistically significant improvements between day 5 and day 33 were the Saline and MNP w. CsA (1.5 µg×1/wk) groups (p<0.05), but comparably, the increased tear production is only at 50% of the initial tear production rate. This phenomenon was also observed in our previous short term treatment study (Liu et al. 2014). Since the dry eye induction procedures (scopolamine and desiccating environment) were maintained throughout the study, their effects were likely too overwhelming for the treatment effects of CsA. Although the tear production improved for MNP w. CsA (1.5 µg×1/wk), the corneal fluorescein staining only improved up to day 19 and gradually worsened toward the end of the study, implying distinct ocular surface damage. To better understand the treatment effects of the immunosuppressant agent, CsA, closer examination of the ocular surface was conducted using histopathology, to identify signs of inflammation and ocular surface integrity.

Example 3: Corneal Fluorescein Staining Analysis of Mice

Corneal fluorescein staining was observed, recorded and photographed with a slit-lamp bio-microscope using a cobalt blue light, 10 minutes after the administration of 1 µl of sodium fluorescein solution (10 mg/ml). On days 5, 12, 19 and 26, before the weekly administrations, corneal fluorescein staining was performed.

The tear volume measurements were also corroborated by the corneal fluorescein staining analysis. All groups (excluding the Healthy control group) showed a similar dryness on the eye: compared to the Healthy group, all groups showed a relatively high amount of fluorescein staining on the corneal surface due to the ocular surface damage inflicted by the dryness induced by the treatment. Only the MNP w. CsA (0.3/0.6 µg×1/wk) group showed an improvement by the end of the study compared to its earlier measurements in terms of corneal fluorescein staining, whereas the MNP w. CsA (1.5 µg×1/wk) group showed improvements up to week 2 (day 19), but showed a worsening effect from day 19 until day 33.

Example 4: Histopathology Analysis of Ocular Tissues of Mice

The eyes were enucleated and collected immediately after euthanasia for histopathological evaluation. The entire upper eyelids were also dissected and collected for evaluation of the tarsal conjunctiva and the underlying soft tissues. Consecutive sections of the entire ocular globe and eyelids were processed for microscopic analysis: After initial fixation in 10% neutral buffered formalin, the tissue was embedded in paraffin, serially sectioned into 5 µm thick sections, and stained with hematoxylin and eosin (H&E). The histological slides were evaluated using bright field microscopy (Leica DM1000, ICC50 HD, Leica Microsystems Inc, Canada).

Figure 4:
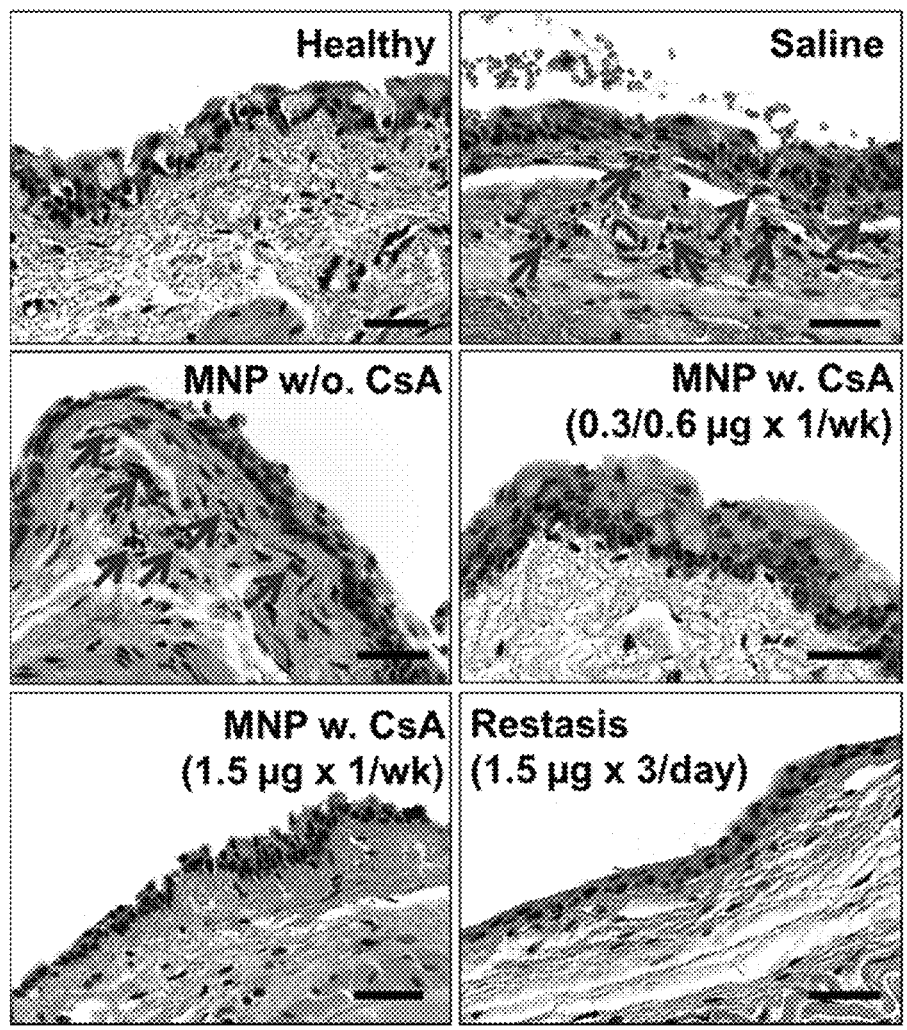
FIG. 4. Histopathology analysis of ocular tissues of mice with different treatment groups. The arrows represent some of the inflammatory infiltrates such as lymphocytes, polymorphonuclears and eosinophils observed. The scale bars are 100 μm in length. MNP w. CsA (0.3/0.6 μg×1/wk) was administered with 0.3 μg of CsA per week for the first two weeks, and with 0.6 μg of CsA per week for the subsequent two weeks.

The ocular tissues of the mice in the Healthy group showed all the signs of healthy eyes. The conjunctival epithelium displayed surface epithelium cells with normal morphology and architecture along with abundant goblet cells which indicated the presence of adequate conditions for production and formation of a stable tear film layer on the surface of the ocular mucous membrane FIG. 4, top left). The lamina propria were composed of loose connective tissues with occasional lymphocytes, and showed no evidence of acute or chronic inflammation. By contrast, in the DES groups treated with both the Saline and MNP w/o. CsA showed conjunctival epithelium and lamina propria changes consistent with disease (FIG. 4, top right and middle left). There were mild to moderate levels of mixed inflammatory infiltrates composed of lymphocytes and occasional polymorphonuclears leucocytes, indicated by the arrows in the figure. The epithelium was thinned out and showed marked reduction, or in some cases, complete absence of goblet cells. The mice treated with MNP w. CsA (0.3/0.6 µg×1/wk) showed conjunctiva with no signs of inflammatory infiltrates (FIG. 4, middle right), displaying morphological features similar to those seen in the Healthy mice group. Moreover, the surface epithelium demonstrated partial to complete recovery of the goblet cells. In terms of the number of goblet cells, the majority of the surface epithelium of the eye samples in this group closely resembled the Healthy group. Similarly, the mice treated with higher dose of CsA loaded NPs (MNP w. CsA (1.5 µg×1/wk)) showed no signs of inflammatory infiltrates (FIG. 4, bottom left). However, the ocular specimens in this group demonstrated a significantly reduced amount of goblet cells on the surface, and in some cases, complete lack of goblet cells. The mice treated with the commercial form of CsA, RESTASIS®, similarly showed no signs of inflammation, but similar to the MNP w. CsA (1.5 µg×1/wk) group, the surface epithelium remained thinned and was completely deprived of goblet cells (FIG. 4, bottom right).

To better understand the treatment effects of the immunosuppressant agent, CsA, closer examination of the ocular surface was conducted using histopathology, to identify signs of inflammation and ocular surface integrity. The ocular tissues of the Saline and MNP w/o. CsA group showed that these formulations were unable to treat the symptoms of DES, demonstrating pronounced inflammation and a complete lack of goblet cells on the ocular surface (FIG. 4). It is possible that MNP w/o. CsA group may further induce inflammation due to the degradation of the PLA chains. However, in our previous study, we showed that the NPs themselves did not cause any inflammation after weekly dosing of up to 12 weeks (Liu et al. 2014). It is likely that the timeframe for NP clearance with the mucous membrane is shorter than that of hydrolytic degradation of the PLA polymers. All three formulations containing CsA (MNP w. CsA (0.3/0.6 µg×1/wk), MNP w. CsA (1.5 µg×1/wk), and Restasis®) showed elimination of inflammatory infiltrates, which is the main function of CsA. However, only the MNP w. CsA (0.3/0.6 µg×1/wk) group showed recovery of the ocular surface in addition to the lack of inflammatory infiltrates. In our previous study, we observed the elimination of inflammation and full recovery of the ocular surface with MNP w. CsA (1.5 µg×1/wk) group for the 1 week treatment study (Liu et al. 2014).

After 4 weeks of treatment, the MNP w. CsA (0.3/0.6 µg×1/wk) showed both the elimination of inflammation and the recovery of the ocular surface while MNP w. CsA (1.5 µg×1/wk) only showed elimination of inflammation without the full ocular surface recovery. We speculate that MNP w. CsA (1.5 µg×1/wk) group likely had sufficient CsA to treat DES in 1 week, but when this dosage was repeated for 4 weeks, the prolonged exposure to this dose may have slowed down or prevented the recovery of the ocular surface. The long term toxicity of CsA on the ocular surface has not been well documented in the past, likely due to rapid ocular clearance of CsA using conventional formulations. We hope to further investigate the long term effect of CsA on ocular surface as a result of mucoadhesion of the drug carriers, especially in terms of recovering the ocular surface tissues.

The mice treated with Restasis® also showed similar effects, likely due to the frequent exposure (thrice daily) to the high concentration CsA in the precorneal tear fluid. Therefore, we believe that it is necessary to lower the dosage of the CsA in the mucoadhesive NPs even further, from 5% of Restasis® (MNP w. CsA (1.5 µg×1/wk)) to 1 to 2% (MNP w. CsA (0.3/0.6 µg×1/wk)), for long term treatment of DES to facilitate the ocular surface recovery without compromising the therapeutic efficacy.

Example 5: Ocular Retention of the Mucoadhesive Nanoparticles on NZW Rabbits

In the first study, we evaluated the effect of PBA on the ocular retention of the PBA modified NPs. Cyanine, with hydrazide functional group, was conjugated to the oxidized dextran through reductive amination, in the similar manner to the PBA conjugation onto dextran. The unreacted PBA and cyanine were removed through multiple methanol wash. We compared the ocular retention of cyanine labelled dextran (Dex-cyanine−PBA) with cyanine labelled dextran-PBA (Dex-cyanine+PBA) using 25 mg/ml solutions.

Secondly, we used ICG as a model drug to estimate the change in its retention time as a result of encapsulation and delivery with PBA-modified NPs. ICG was encapsulated in the NPs using the same nanoprecipitation method that was used to encapsulate CsA. ICG encapsulated NPs were then dialyzed to remove free ICG and DMSO. We also evaluated the retention of ICG encapsulated in unmodified NPs to further evaluate the effect of PBA on the ocular retention. We compared the ocular retention of free ICG or ICG encapsulated in unmodified NPs (NP-ICG−PBA) with ICG encapsulated in PBA modified NPs (NP-ICG+PBA).

NZW male rabbits were sedated with acepromazine (2 mg/kg) and briefly anesthetized using a mask with 2% isoflurane for 10 minutes for eye drop instillation. For each rabbit, one eye was administered with 50 µL of sample formulations (Dex-cyanine+PBA or NP-ICG+PBA) while the contralateral eye was administered with 50 µL of control formulations (Dex-cyanine−PBA, Free ICG or NP-ICG−PBA). We used confocal scanning laser ophthalmoscopy (cSLO; Spectralis®: Heidelberg Retinal Angiography 2, Heidelberg Engineering, Germany) for imaging at baseline before administration and at 0, 3, 6, 9 and 24 hrs after the initial administration. After imaging at each time point, rabbits were transferred back to their cages to blink normally. To image cyanine or ICG, we used an excitation wavelength of 795 nm and an emission wavelength at 810 nm for all images. To achieve standardized images, the power and sensitivity were routinely set at 100% and 90 units, respectively, and the relative brightness of the ocular surface images were analyzed using ImageJ. An eclipse was drawn on the ocular surface to enclose as much area as possible while avoiding the bright edges between the corneal surface and the eyelids where dye/particles accumulate due to pooling. The average brightness of the area inside the eclipse was measured and the background signal was subtracted from it. All of the means of the fluorescence measurements were normalized with respect to the initial mean fluorescence measurements at time 0 hr, right after instillation of the eye drops.

Figure 5:
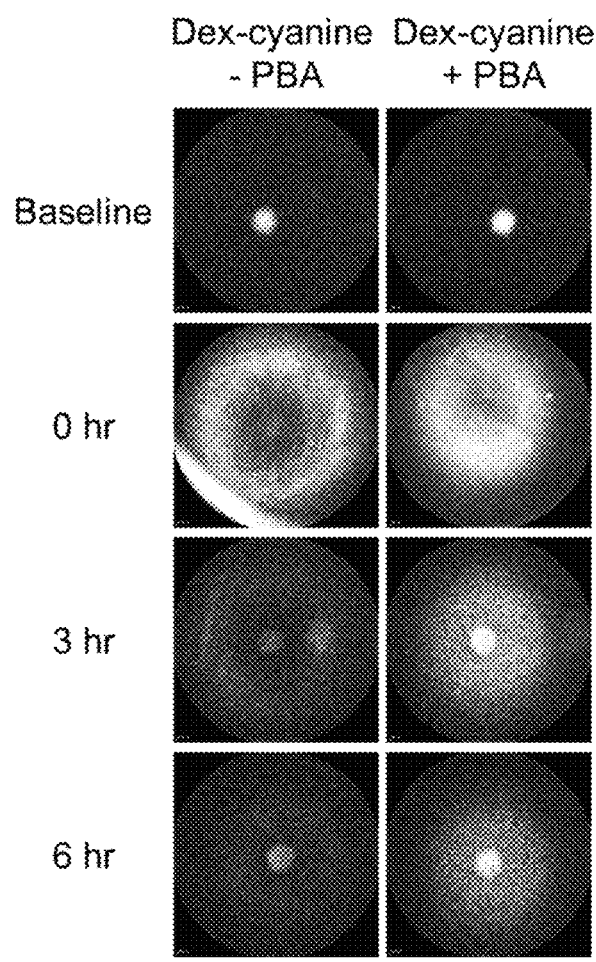
FIG. 5. Ocular retention of shell material of the MNPs on NZW rabbits. Images of rabbit eyes treated with cyanine labelled dextran (Dex-cyanine−PBA) and PBA-dextran (Dex-cyanine+PBA) were obtained with confocal Scanning Laser Ophthalmoscope (cSLO), $\lambda_{ex}$=795 nm and $\lambda_{em}$=810 nm.
Figure 6:
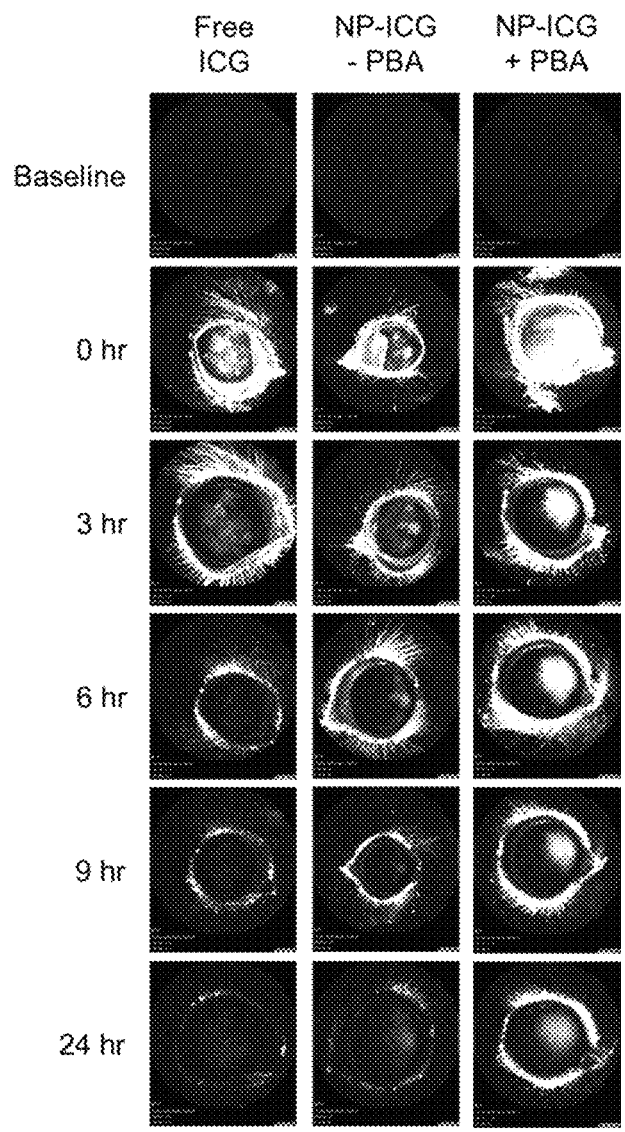
FIG. 6. Ocular retention of drugs delivered through MNPs on NZW rabbits. Indocyanine green (ICG), a near infrared fluorescent dye, was used as a model drug. ICG was encapsulated in MNPs. Images of NZW rabbit eyes treated with Free ICG, NP-ICG (−PBA), and NP-ICG (+PBA) obtained with cSLO, $\lambda_{ex}$=795 nm and $\lambda_{em}$=810 nm. Note that NP-ICG (−PBA) represent the nanoparticles without the mucoadhesive targeting ligand, PBA, while the NP-ICG (+PBA) is equivalent to the MNPs described throughout the document.
Figure 7:
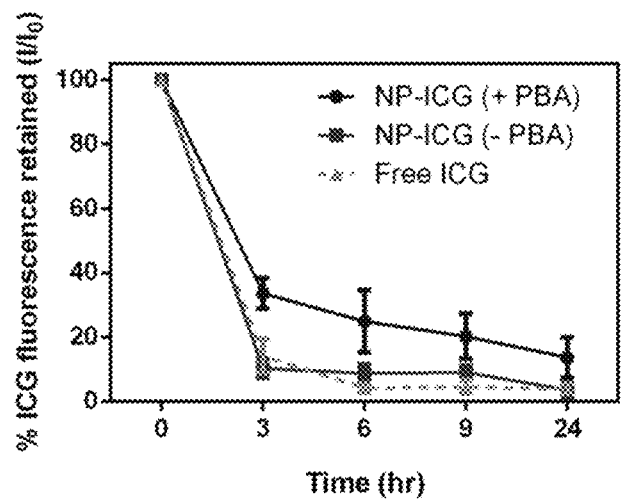
FIG. 7. ImageJ analysis of the fluorescence of the images obtained using cSLO for ICG delivered through MNPs. Quantitative analysis of the images taken from rabbit eyes treated with Free ICG, NP-ICG (−PBA) and NP-ICG (+PBA) (n=3; mean±s.e.m.). I: fluorescence brightness measured using ImageJ software; 10: initial fluorescence brightness (at 0 hr). Note that NP-ICG (−PBA) represent the nanoparticles without the mucoadhesive targeting ligand, PBA, while the NP-ICG (+PBA) is equivalent to the MNPs described throughout the document.
Figure 8:
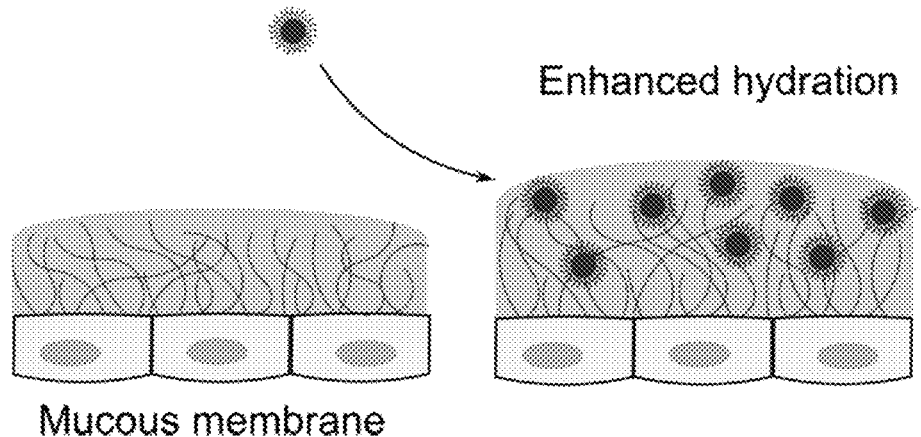
FIG. 8. Schematic illustration of enhanced hydration of mucous membranes as a result of binding of mucoadhesive nanoparticles. The delivery of mucoadhesive nanoparticles with hydrophilic surfaces to the mucous membrane may enhance the hydration of the mucous membrane.

To analyze the effect of PBA on the in vivo ocular retention of the NPs, Cyanine labelled dextran-PBA, the shell material of the NPs and Cyanine labelled dextran were compared using cSLO imaging. PBA modified dextran showed clear retention for up to 6 hrs after the initial eye drop administration, whereas the unmodified dextran showed negligible amount of retention 3 hrs and 6 hrs after the initial administration (FIG. 5). Furthermore, ICG was used as a model drug for imaging the corneal surface of rabbit eyes using cSLO. Standardized cSLO images (FIG. 6) showed that the ICG delivered using NPs (NP-ICGs+PBA) demonstrated higher retention of ICG compared to the ICG control, which was especially noticeable at the 6 hr timepoint (FIG. 6): up to 24.9% of the initial ICG from NP-ICGs administration was still retained after 6 hrs whereas only about 4.26% of the ICG was retained after administration of Free ICG (FIG. 7). 24 hrs after the initial administration, NP-ICG+PBA retained up to 13.7% of the initial brightness, whereas Free ICG remained near baseline level of 4.01%. The unmodified NPs encapsulating ICG (NP-ICG−PBA) showed similar ocular clearance rate of ICG as that of the Free ICG.

We demonstrated prolonged retentions of both the PBA modified NP shells and the model drug delivered through PBA modified NPs using fluorescence imaging using in vivo studies. We first showed that the shell material of the nanoparticles, PBA modified dextran, showed improved retention compared to unmodified dextran for up to 6 hrs based on qualitative observation, demonstrating the mucoadhesive properties of PBA molecules. We also demonstrated the prolonged retention of the model drug, ICG, when delivered with PBA modified NPs in vivo compared against an aqueous solution ICG encapsulated in NPs showed increased retention on the surface of rabbit eyes for up to 24 hrs using quantitative analysis (FIG. 4). Considering the rapid clearance of Restasis® from the ocular surface within the first 20 minutes of eye drop administration. These data demonstrate that PBA modified NPs may significantly prolong the ocular retention of loaded therapeutics by attaching to the ocular mucous membrane. Previous studies demonstrated improved retention of CsA by encapsulating them in non-PBA NPs but the CsA concentration in the lachrymal fluid quickly reached baseline levels after the first few hours (Cholkar et al. 2013). This study further corroborates the previous in vitro data showing mucoadhesive properties of the PBA modified NPs due to covalent linkage to mucin (Liu et al. 2012).

The above-described embodiments are intended to be examples only. Alterations, modifications and variations can be effected to the particular embodiments by those of skill in the art. The scope of the claims should not be limited by the particular embodiments set forth herein, but should be construed in a manner consistent with the specification as a whole.

All references cited in this document are incorporated herein by reference in their entirety.

REFERENCES

Verma M S, Liu S, Chen Y Y, Meerasa A, Gu F X. Size-tunable nanoparticles composed of dextran-b-poly (D,L-lactide) for drug delivery applications. Nano Res. 2012; 5:49-61.

Liu S, Jones L, Gu F X. Development of mucoadhesive drug delivery system using phenylboronic acid functionalized poly(D,L-lactide)-b-dextran nanoparticles. Macromol Biosci. 2012; 12:1622-1626.

Liu S, Chang C N, Verma M, et al. Phenylboronic acid modified mucoadhesive nanoparticle drug carriers facilitate weekly treatment of experimentally-induced dry eye syndrome. Nano Res. 2014:8:621-635.

Cholkar K, Patel S P, Vadlapudi A D, Mitra A K. Novel strategies for anterior segment ocular drug delivery. Journal of Ocular Pharmacology and Therapeutics 2013; 29:106-123. Pflugfelder S.C. Antiinflammatory Therapy for Dry Eye; Am J Ophthalmol 2004; 137:337-342.

Sall K, Stevenson O D, Mundorf T K, Reis B L, CsA Phase 3 Study Grp. Two multicenter, randomized studies of the efficacy and safety of cyclosporine ophthalmic emulsion in moderate to severe dry eye disease. Ophthalmol. 2000; 107:631-639.

Barber L D, Pflugfelder S C, Tauber J, Foulks G N. Phase III safety evaluation of cyclosporine 0.1% ophthalmic emulsion administered twice daily to dry eye disease patients for up to 3 years. Ophthalmology 2005; 112:1790-1794.

What is claimed is:

1. A method for treating a disease or condition involving inflammation, comprising topically administering to the anterior surface of an eye of a subject a composition comprising nanoparticles capable of releasing cyclosporine A, the nanoparticles comprising a plurality of linear amphiphilic PLA-b-Dex diblock copolymers and being functionalized with phenylboronic acid (PBA), wherein the concentration of cyclosporine A in the composition is about 0.001% to about 0.1% wt/vol.

2. The method of claim 1, wherein the copolymers comprise PLA-b-Dex-g-PBA.

3. The method of claim 1, wherein the nanoparticles have an average particle size of less than about 1000 nm, less than about 100 nm, less than about 50 nm, or less than about 30 nm.

4. The method of claim 1, wherein the disease or condition is dry eye syndrome.

5. The method of claim 1, wherein the composition is administered at a dose and/or administration frequency that provides a therapeutic effect while substantially preserving the function and integrity of the mucosal lining.

6. The method of claim 1, wherein the composition is administered at a dose and/or administration frequency that improves hydration of the mucosal lining.

7. The method of claim 1, wherein the composition is formulated as an aqueous suspension.

8. The method of claim 1, wherein the concentration of cyclosporine A in the composition is about 0.01 to about 0.1% wt/vol or about 0.01% to about 0.05% wt/vol.

9. The method of claim 1, wherein the cyclosporine A is administered at a dose of about 0.1 µg to about 125.0 µg per week, about 0.1 µg to about 100.0 µg per week, about 0.1 µg to about 75.0 µg per week, about 0.1 µg to about 50.0 µg per week, about 0.1 to about 20.0 µg per week, about 0.1 to about 10.0 µg/week, about 0.1 to about 5.0 µg/week.

10. The method of claim 1, wherein the composition is administered once every 1, 2, 3, 4, 5, 6, 7, 8, 9, 10, 11, 12, 13, 14, 15, 16, 17, 18, 19 or 20 days.

11. The method of claim 1, wherein the composition is administered once per week.

12. The method of claim 1, wherein the composition is administered at an overall dose of less than about 150.0 µg per week at an administration frequency of less than 10 times per week.

13. The method of claim 1, wherein the composition is administered less than 5 times per week.

14. The method of claim 1, wherein the composition is administered less than 2 times per week.

15. The method of claim 1, wherein the composition is administered at an overall dose of about 0.1 µg to about 75.0 µg cyclosporine A per week.

16. The method of claim 1, wherein the composition is administered at an overall dose of about 0.1 µg to about 20.0 µg cyclosporine A per week.

17. The method of claim 1, wherein the composition is administered once every 1, 3, 7 or 14 days.

18. The method of claim 1, wherein the surface density of PBA is about 1 per $nm^2$ to 15 per $nm^2$.

19. The method of claim 1, wherein the nanoparticles have an average particle size of less than about 100 nm.

20. A method for treating a disease or condition involving inflammation, comprising topically administering to the anterior surface of an eye of a subject a composition comprising nanoparticles capable of releasing cyclosporine A, the nanoparticles comprising copolymers consisting essentially of linear amphiphilic PLA-b-Dex diblock copolymers and being surface-functionalized with phenylboronic acid (PBA), wherein the concentration of cyclosporine A in the composition is about 0.001% to about 0.1% wt/vol, and wherein the composition is administered at an overall dose of about 0.1 µg to about 20.0 µg cyclosporine A per week at an administration frequency of less than 10 times per week.

* * * * *